(12) United States Patent
Komaki

(10) Patent No.: US 10,602,953 B2
(45) Date of Patent: Mar. 31, 2020

(54) ELECTRO-OCULOGRAPHIC DETECTOR AND ELECTRO-OCULOGRAPHIC DETECTION METHOD

(71) Applicant: Kabushiki Kaisha Toshiba, Minato-ku, Tokyo (JP)

(72) Inventor: Hiroaki Komaki, Tachikawa Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 823 days.

(21) Appl. No.: 15/253,077

(22) Filed: Aug. 31, 2016

(65) Prior Publication Data

US 2017/0150897 A1 Jun. 1, 2017

(30) Foreign Application Priority Data

Nov. 27, 2015 (JP) .................. 2015-232083

(51) Int. Cl.
A61B 5/0496 (2006.01)
A61B 3/113 (2006.01)
A61B 5/00 (2006.01)
A61B 5/11 (2006.01)

(52) U.S. Cl.
CPC ............ *A61B 5/0496* (2013.01); *A61B 3/113* (2013.01); *A61B 5/6803* (2013.01); *A61B 5/1103* (2013.01); *A61B 2560/0223* (2013.01); *A61B 2562/0219* (2013.01)

(58) Field of Classification Search
CPC ..... A61B 3/113; A61B 5/0496; A61B 5/6803; A61B 5/6821
See application file for complete search history.

(56) References Cited

U.S. PATENT DOCUMENTS

| | | | |
|---|---|---|---|
| 5,360,971 A | * | 11/1994 | Kaufman ............... A61B 3/113 250/221 |
| 8,449,116 B2 | | 5/2013 | Sato et al. |
| 9,433,369 B2 | | 9/2016 | Kanoh et al. |
| 2011/0178784 A1 | | 7/2011 | Sato et al. |
| 2013/0324881 A1 | | 12/2013 | Kanoh et al. |
| 2016/0132107 A1 | | 5/2016 | Kanishima et al. |

FOREIGN PATENT DOCUMENTS

| | | |
|---|---|---|
| JP | 2006-340986 | 12/2006 |
| JP | 2009-288529 A | 12/2009 |
| JP | 2011-125693 A | 6/2011 |
| JP | 2013-244370 A | 12/2013 |
| JP | 5490664 B2 | 5/2014 |
| JP | 2014-124308 A | 7/2014 |

\* cited by examiner

*Primary Examiner* — Eun Hwa Kim
(74) *Attorney, Agent, or Firm* — Knobbe, Martens, Olson & Bear, LLP

(57) ABSTRACT

According to one embodiment, at least four EOG electrodes are provided with the periphery of user's eyes. The left eye side electrodes and the right eye side electrodes are arranged symmetrically with respect to a vertical line passing the middle of a line connecting the centers of both eyes. Two electrodes above and two electrodes below the line connecting the centers of both eyes are arranged to avoid area AXL including an inflection point where an EOG detection polarity differs in the right and left of a vertical line passing the center of the left eye and area AXR including an inflection point where an EOG detection polarity differs in the right and left of a vertical line passing the center of the right eye.

4 Claims, 20 Drawing Sheets

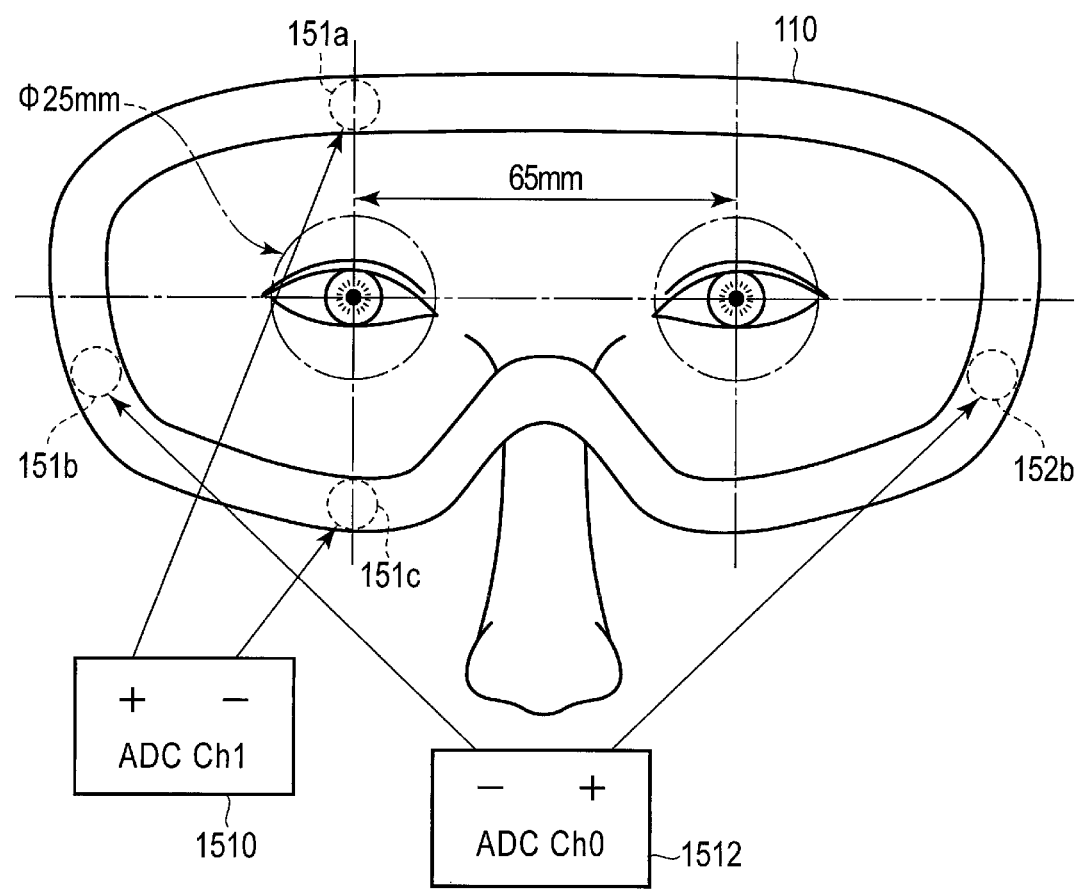
F I G. 5

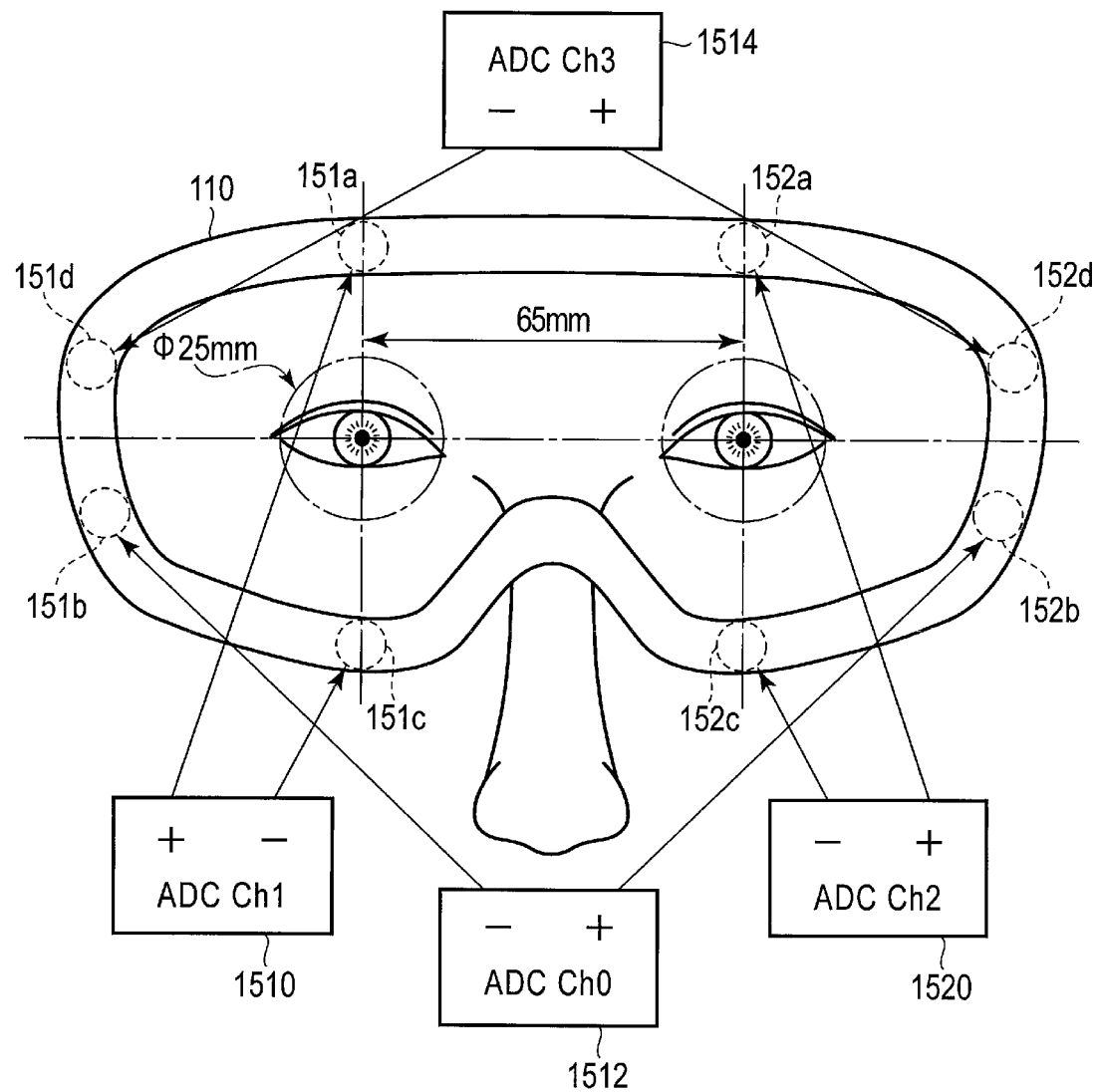
F I G. 6

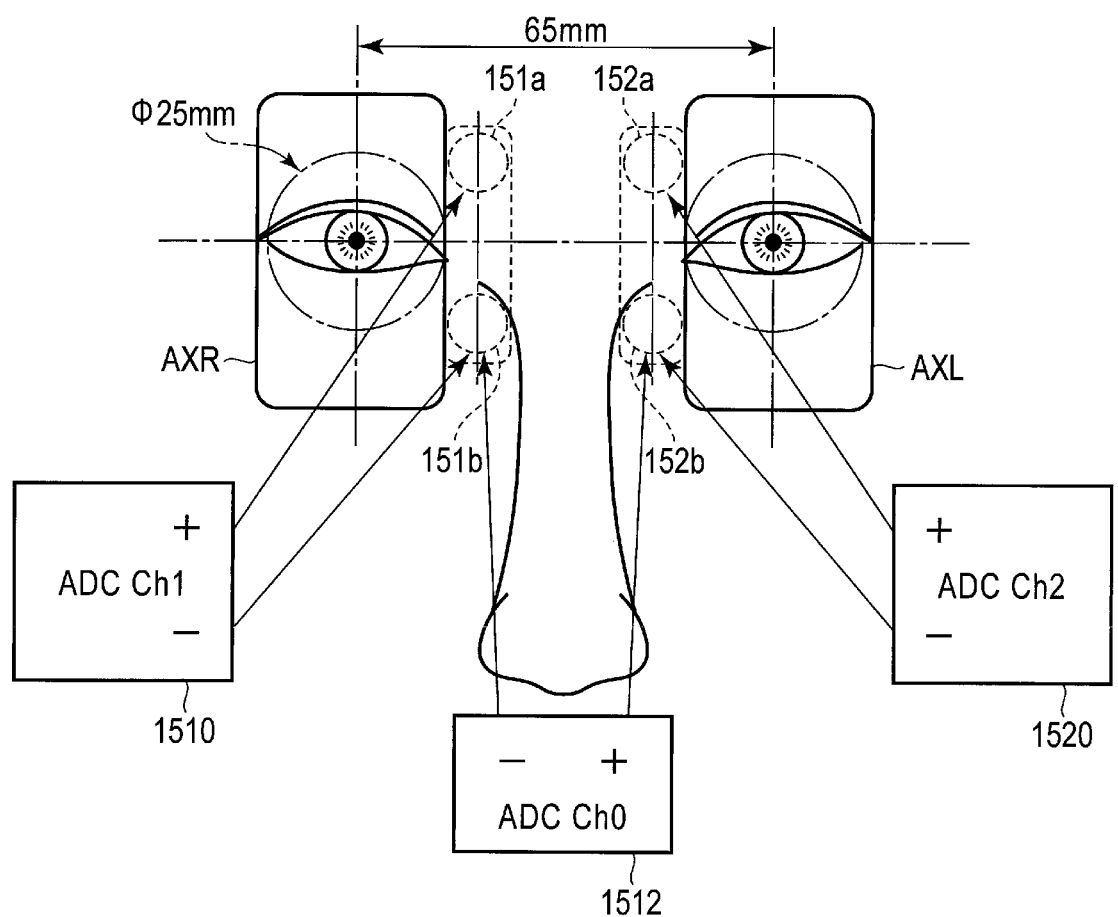
F I G. 7

Vertical axis represents ADC outputs, and scale (= 20000) indicates approximately 4 mV (20000 × 196.695 nV ≈ 4 mV)
Horizontal axis represents time, and indicates number of samples of 256 fs (difference between numbers of horizontal axis/256 = seconds)

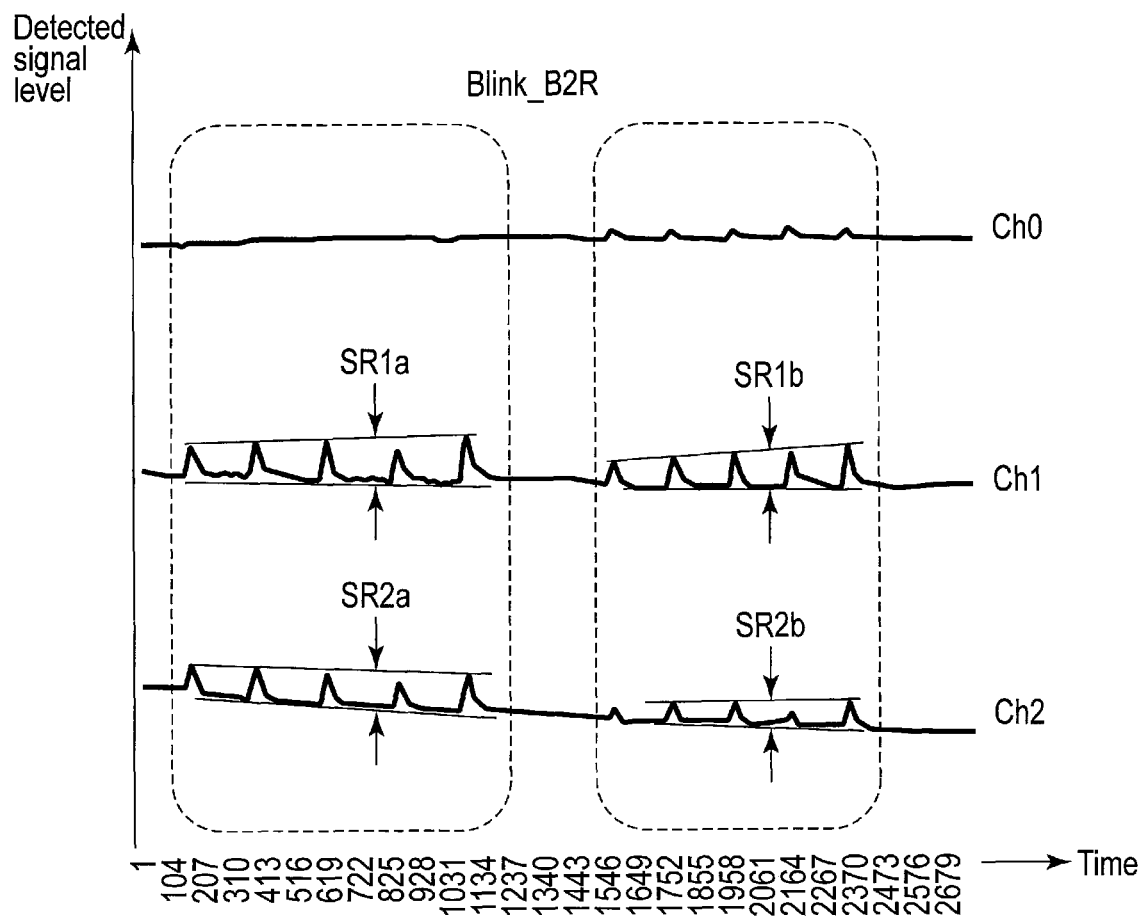
Vertical axis represents detection signal level and horizontal axis represents time
(target range is within dotted-line, 256 fs)
EOG measured for five blinks (rapid) and five right winks
F I G. 16

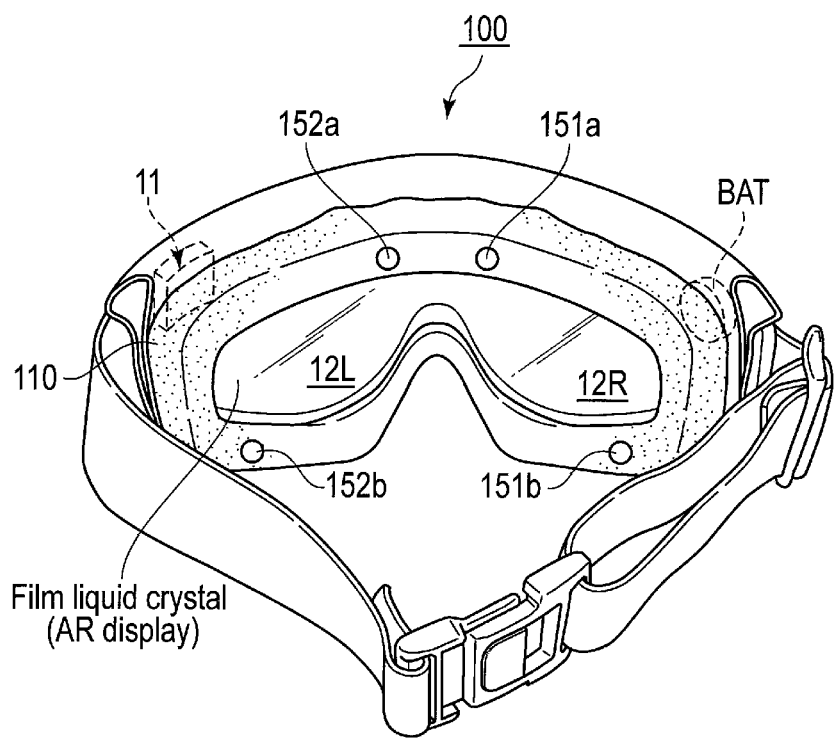
F I G. 20
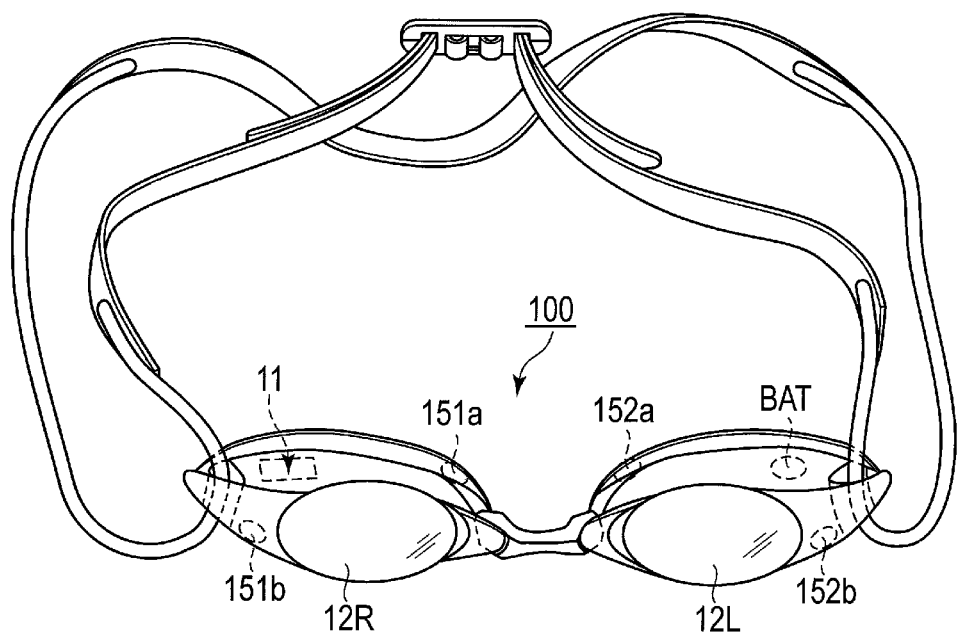
F I G. 21

ELECTRO-OCULOGRAPHIC DETECTOR AND ELECTRO-OCULOGRAPHIC DETECTION METHOD

CROSS-REFERENCE TO RELATED APPLICATIONS

This application is based upon and claims the benefit of priority from Japanese Patent Application No. 2015-232083, filed Nov. 27, 2015, the entire contents of which are incorporated herein by reference.

FIELD

Embodiments described herein relate generally to a device which detects an electro-oculograph whose variations correspond to the movement of the eye, the eye being electrically charged, and a method for such detection.

BACKGROUND

There has been proposed a technique of using an electro-oculograph produced by a person's eye movements to identify an area being observed by the person. In this proposal (referred to as proposal 1), electro-oculographic (EGG) electrodes are used to detect the electro-oculograph. Area-of-observation identifiers include a detector which detects the position of the eyes on the basis of the electro-oculograph of the eye movements, and an extractor which, using the detected position of eyes as a reference, extracts from a predetermined area in an image being viewed by the user the area being observed. In proposal 1, while electro-oculography is used to detect the position of eyes, such ocular actions (eye-motion) as vertical and horizontal eye movements, blinking and closing of the eyes, and winking are not distinguishably detected. Thus, such eye movements are not used as data input to a computer.

There has also been proposed a technique of distinguishably detecting various eye movements with an eyewear. In this proposal (referred to as proposal 2), the eyewear takes the form of glasses which include EOG electrodes on the nose pads and the bridge between the lens frames (the part which spans the bridge of the nose) to detect electro-oculographic changes corresponding to the movements of the wearer's eyes. The way in which the electro-oculograph changes depends on the ocular actions (eye-motion) of the wearer (vertical or horizontal movement, blinking, and so on). Using this mechanism, the user can input data corresponding to the variations of eye movements to a computer or the like.

In proposal 2, because the EOG electrodes are provided on the nose pads, the detected electro-oculograph is weak and easily degraded by ambient noise. Therefore, highly accurate detection of eye movement or eye direction becomes difficult to perform based on such a degraded electro-oculograph. If the electro-oculograph becomes stronger, the dynamic range between the noise floor and the peak level of the detected signal increases. In such a wide dynamic range, a plurality of threshold values can be set, and the variety of detection data can be increased by the number of threshold values. In other words, a stronger electro-oculograph is not easily degraded and allows highly accurate detection of various eye movements.

If the electrode arrangement of proposal 1 could be adopted, a stronger electro-oculograph would be detected than is detected in proposal 2. However, the EOG arrangement of proposal 1 is completely different from that of proposal 2 and cannot be simply applied to the nose pads of proposal 2. Therefore, application of the EOG arrangement of proposal 1 (stronger electro-oculograph) to the lens frame of proposal 2 (which can be used in detection of various eye movements) to facilitate the detection performance of the lens frame of proposal 2 is not easily conceivable.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 5 shows a second example of electrode implementation of an electro-oculographic detector of the third embodiment (goggles).

FIG. 6 shows an example of electrode implementation of an electro-oculographic detector of a fourth embodiment (goggles).

FIG. 7 shows an example of electrode arrangement of an electro-oculographic detector of a fifth embodiment (glasses).

FIG. 9 is a view being viewed from the face of a user.

FIG. 10 is a view being viewed from the face of a user.

FIG. 16 shows an example of waveforms of an electro-oculograph obtained when the eyes directed ahead are blinked five times and the right eye winked five times (blinking of the right eye).

FIG. 20 is an example of optical head-mounted display goggles (in which the lens frames of both eyes are formed continuously) including a cushion on a surface contacting the face of a user and electro-oculographic detection electrodes provided with appropriate positions on the cushion (as in FIG. 1), the optical head-mounted display being viewed from the rear.

FIG. 21 is an example of optical head-mounted display goggles (in which the lens frames of both eyes are separated) including electro-oculographic detection electrodes provided with appropriate positions on the surface contacting the face of a user (as in FIG. 1).

DETAILED DESCRIPTION

Embodiments will be described hereinafter with reference to the accompanying drawings.

Embodiments may be used to detect a stronger electro-oculograph to facilitate highly accurate detection of various eye movements (or eye-motions).

In an electro-oculographic detector according to an embodiment, at least four EOG electrodes may be arranged around both eyes of a user as follows (cf. FIG. 2). Two electrodes on the left eye side (152a and 152b) and two electrodes on the right eye side (151a and 151b) are arranged symmetrically with respect to a vertical line (a nose line along the nasal crest of the user) passing the middle point of the line connecting the centers of both eyes. Two electrodes above the line connecting the centers of both eyes (151a and 152a) and two electrodes below the line connecting the centers of both eyes (151b and 152b) are arranged to avoid a predetermined left area (AXL) and a predetermined right area (AXR). The predetermined left area (AXL) includes an inflection point where a detection polarity of the electro-oculograph differs in the right and left of a vertical line passing the center of the left eye (P1). The predetermined right area (AXR) includes an inflection point where a detection polarity of the electro-oculograph differs in the right and left of a vertical line passing the center of the right eye (P2).

<Basic Data>

Adults have eyeballs of approximately 25 mm diameter. Infants have eyeballs of approximately 17 mm diameter which grow with time.

A gap between pupils of an adult male is approximately 65 mm (a commercially available stereo camera is often made with a gap of 65 mm between lenses thereof).

The gap between the pupils of an adult female is a few millimeters shorter than that of an adult male.

Eyeballs are electrically charged with a few tens of millivolts.

The eye has a positive potential in the vicinity of the cornea and a negative potential in the vicinity of the retina. If measured on the skin surface, the potential difference therebetween is a few hundred microvolts.

Figure 1:
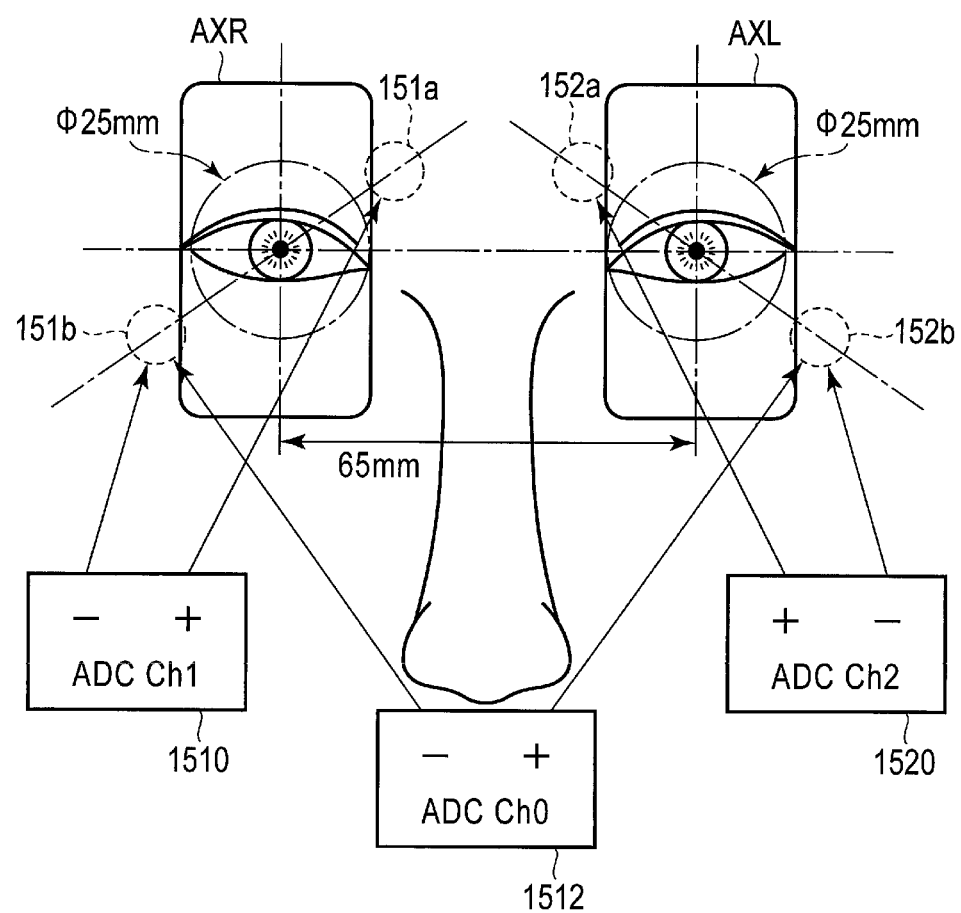
FIG. 1 shows an example of electrode arrangement of an electro-oculographic detector of a first embodiment.

FIG. 1 shows an example of electrode arrangement (ideal arrangement) of an electro-oculographic detector of a first embodiment. FIG. 1 shows a human face being viewed from the direct front and the eye on the right side is the left eye and the eye on the left side is the right eye.

The following description assumes that an adult eyeball is approximately 25 mm in diameter and that the gap between the eyes is approximately 65 mm. The cornea of each eye is positively charged and its retina is negatively charged. The resulting potential difference produces an electric field around the eyeball (or changes a condition of an electric flux line) which changes according to various ocular actions (eye-motion) (such as vertical and horizontal eye movements, blinking and closing of both eyes, and winking of either eye). Changes in the electric field corresponding to various eye movements can be distinguishably detected from one or more channel signals extracted from a plurality of EGG electrodes (151a, 151b, 152a, and 152b) arranged around the eyes.

Specifically, a potential difference between the right and left electrodes below the horizontal line connecting the center of both eyes (151b and 152b) is detected as a first channel signal (Ch0), a potential different between upper and lower electrodes on the right eye side (151a and 151b) (electrodes on the left side of the figure) is detected as a second channel signal (Ch1), and a potential difference between upper and lower electrodes on the left eye side (152a and 152b) is detected as a third channel (Ch2). The first to third channel signals are detected as analogue signals which are later digitized separately through three analog-to-digital converters (ADC Ch0 to Ch2) 1512, 1510, and 1520.

Figure 11:
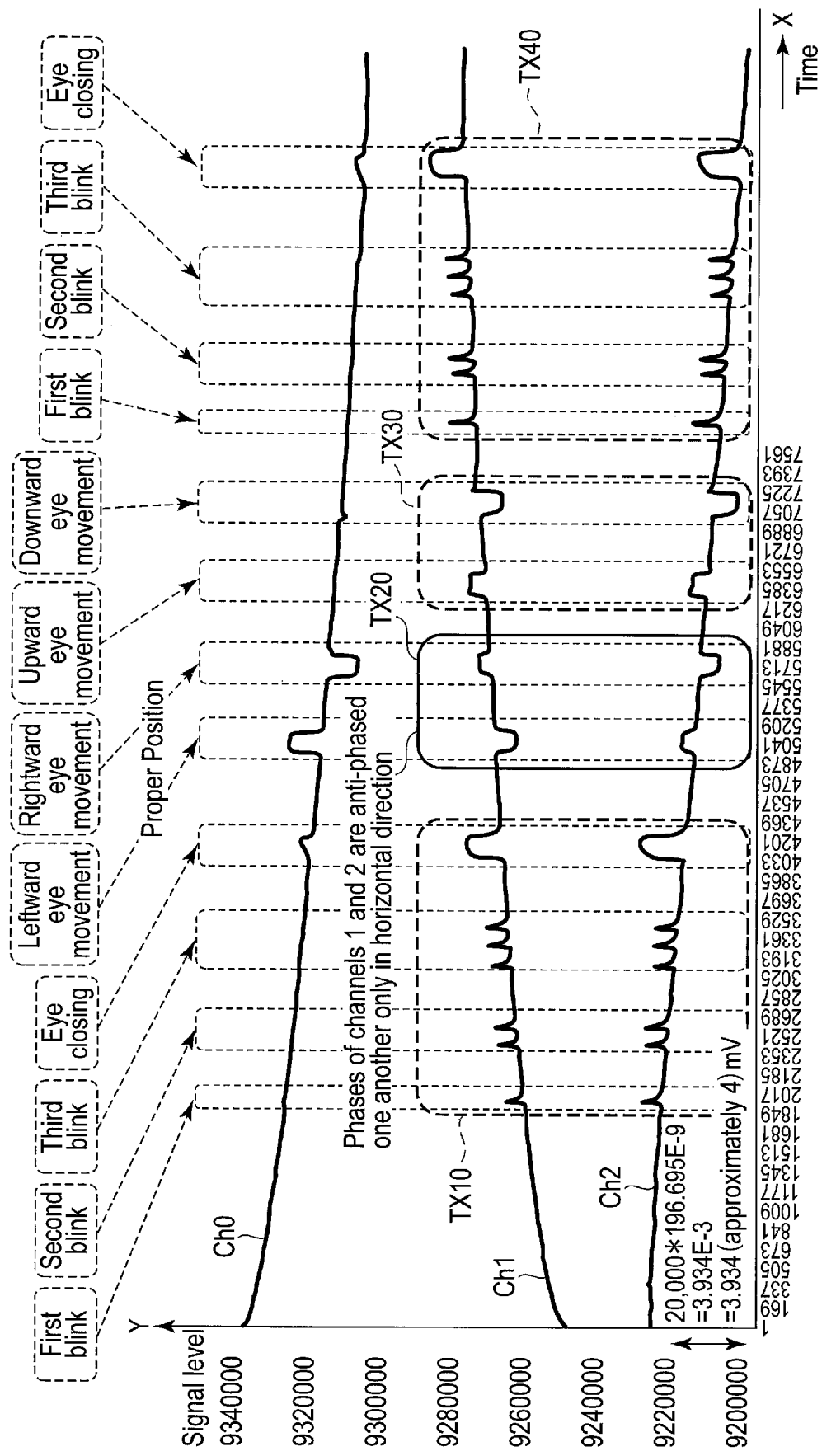
FIG. 11 shows an example of waveforms of an electro-oculograph (EGG) obtained through various ocular actions (blinking, closing of the eyes, and vertical and horizontal eye movements).

Ocular actions (eye-motion) such as blinking and closing of the eyes can be distinguishably detected from signal waveforms of the second channel and/or third channels (Ch1/Ch2) (cf. period TX10 or TX40 in FIG. 11).

Vertical eye movement (upward or downward eye movement) can be distinguishably detected from signal waveforms of the second and/or third channels (Ch1/Ch2) (cf. period TX30 in FIG. 11).

Horizontal eye movement (rightward or leftward eye movement) can be distinguishably detected from signal waveforms from the first channel (Ch0), the second channel (Ch1), or the third channel (Ch2) (cf. period TX20 in FIG. 11).

According to the electrode arrangement and the connection polarity of ADCs in FIG. 1, changes in the signal (horizontal AC components) of Ch1 and changes in the signal (horizontal AC components) of Ch2 show an anti-phase (or reverse phase) relationship with respect to horizontal eye movements (rightward and leftward eye movements). Thus, if the horizontal AC components of Ch1 and Ch2 are added (it means subtraction of same horizontal components), they are canceled. On the other hand, the signal change (vertical AC components) of Ch1 and the signal change (vertical AC components) of Ch2 show an in-phase relationship with respect to vertical eye movements (upward and downward eye movements). Thus, if the vertical AC components of Ch1 and Ch2 are added, they are increased. Using the above, signals can be detected in Ch1 and Ch2 without mutual interference between the changes in the signal of the horizontal movements and the changes in the signals of the vertical movements (that is, highly accurate detection of vertical eye movements can be performed in Ch1 and Ch2).

Furthermore, according to the electrode arrangement and the connection polarity of ADCs in FIG. 1, changes in the potentials of both eyes are added in series and input in ADC 1512 of Ch0 with respect to the horizontal eye movements (rightward and leftward eye movements). Thus, the signal amplitude of the first channel (Ch0) becomes particularly great with respect to the horizontal eye movement detection (cf. period TX20-1 in FIG. 12). Furthermore, the signal waveform of the first channel (Ch0) hardly shows signal components other than that of the horizontal eye movements. Thus, the signals from the first channel (Ch0) are suitable for the detection of horizontal eye movements.

Signals of the first channel (Ch0) have a great amplitude range between the noise floor and the peak level of detection signals, and a plurality of threshold values can be set within such a great amplitude range. The variety of detection data can be increased by the number of threshold values. In other words, the signals are not easily affected by the noise and can be utilized in highly accurate detection of various eye movements.

Note that, in the embodiment of FIG. 1, EOG electrodes around the eyes (151*a*, 151*b*, 152*a*, and 152*b*) are arranged to avoid a predetermined left area (AXL) and a predetermined right area (AXR). The predetermined left area (AXL) includes an inflection point where the polarity of the electro-oculograph differs in the right and left of a vertical line passing the center of the left eye (as a result, a signal phase of each of Ch1 to Ch2 is reversed). The predetermined right area (AXR) includes an inflection point where the polarity of the electro-oculograph differs in the right and left of a vertical line passing the center of the right eye (as a result, a signal phase of each of Ch1 and Ch2 is reversed).

Because of the inflection point, a phase of detection signal components (horizontal components) of the embodiment (shown in FIGS. 1 to 6, etc.) in which right and left electrodes (151*b* and 152*b*) are outside the predetermined right and left areas (AXR and AXL) and a phase of detection signal components (horizontal components) of the embodiment (shown in FIG. 7, etc.) in which right and left electrodes (151*b* and 152*b*) are inside the predetermined right and left areas (AXR and AXL) are reversed.

Figure 2:
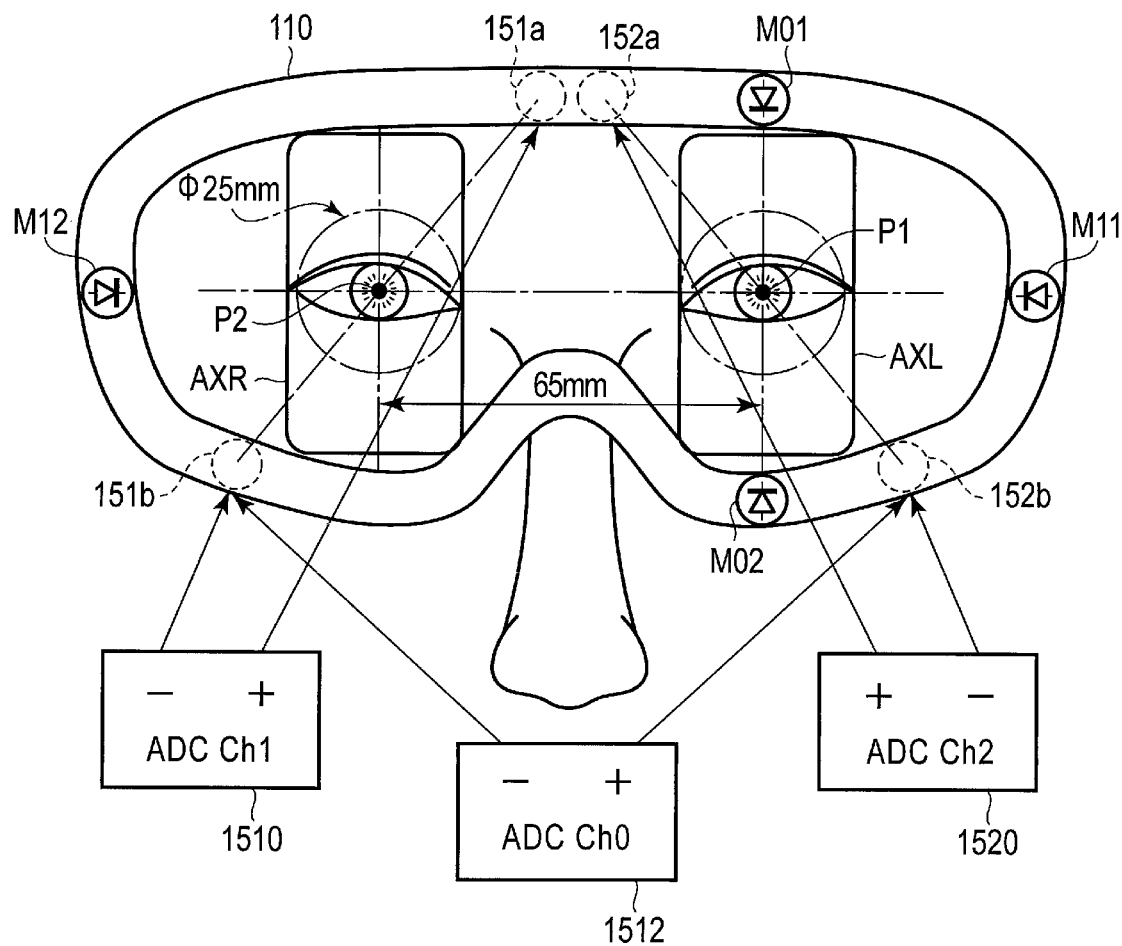
FIG. 2 shows an example of electrode implementation of an electro-oculographic detector of the first embodiment (goggles).

FIG. 2 shows an example of electrode implementation of the electro-oculographic detector of the first embodiment (goggles). In the example of electrode implementation, electrodes are arranged as in FIG. 1 on a cushion surface of an goggles (the surface touching the skin of the user's face).

A silicon cushion or the like is formed on a frame 110 of the goggles and electro-oculographic detection electrodes (EOG electrodes 151*a*, 151*b*, 152*a*, and 152*b*) are attached to positions on the cushion as depicted. The silicon cushion is elastically deformable to correspond to the shape of the face of the user such that all EOG electrodes stably contact the skin surface of the user.

Furthermore, four LEDs (M01, M02, M11, and M12) are attached to the frame 110 of the goggles. Furthermore, centermarkers are arranged in the direct front of each of both eyes (positions P1 and P2) to guide the user to look straight. The centermarkers are, for example, put on certain positions (positions P1 and P2) of a transparent plastic plate fit in the frame 110 through a scribe process. When light from the LEDs on the frame 110 contacts the centermarkers, the light partly diffuses at the centermarkers and bright spots which are recognizable by the user are created.

If a display such as film liquid crystal or the like is provided with the transparent plate inside the frame 110, an augmented reality (AR) display can be realized in which various data items are added to the view of the real world through the goggles. The markers (M01, M02, M11, M12, P1, and P2) can be presented to the user through the AR display.

Figure 18:
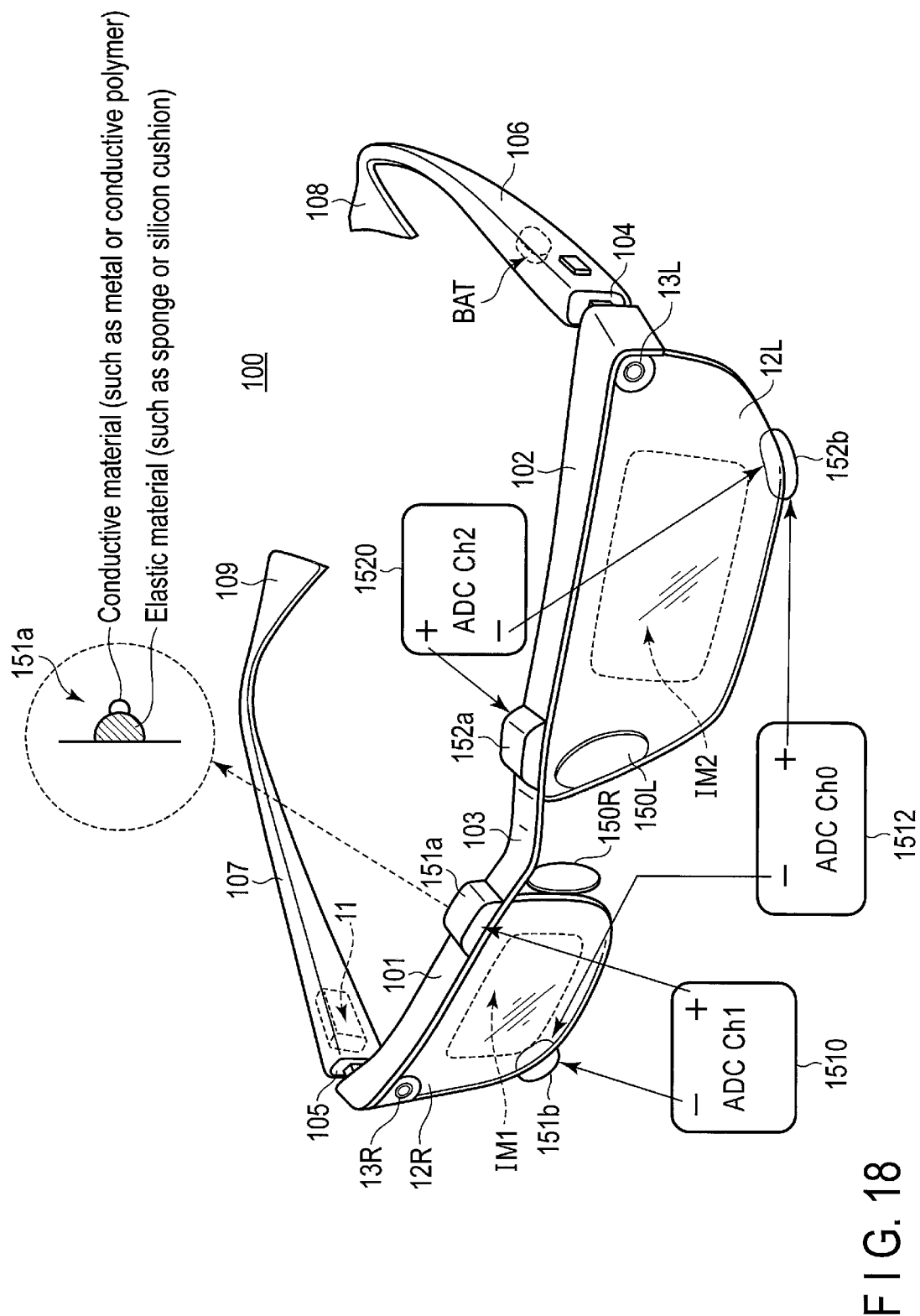
FIG. 18 shows optical head-mounted display glasses in which electro-oculographic detection electrodes are provided with appropriate positions (as in FIG. 1, etc.).

The electrode arrangement example of FIGS. 1 and 2 is appropriate for goggles (as in FIGS. 20 and 21, etc.) but may be applied to glasses (as in FIG. 18, etc.). Furthermore, the electrode arrangement example of FIG. 1 can be applied to other devices. For example, although this is not depicted, the frame 110 of FIG. 2 can be applied to eyepieces of binoculars, binocular microscopes, and industrial periscopes.

Figure 3:
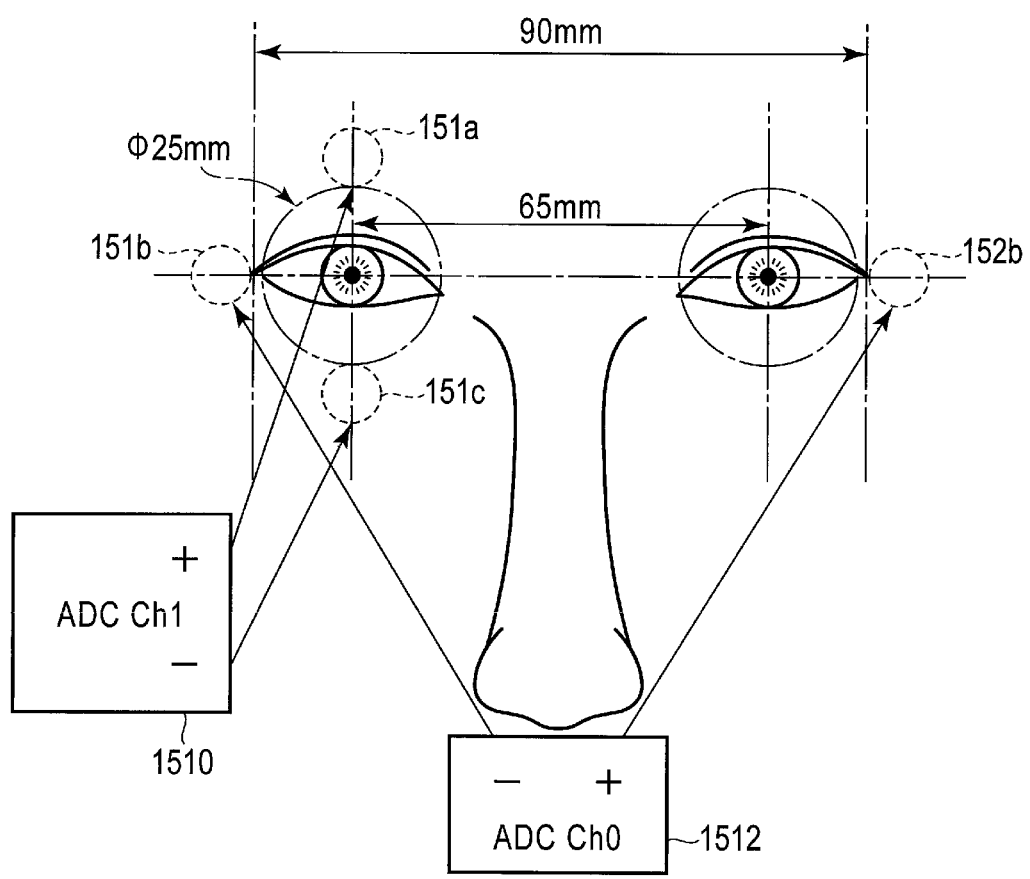
FIG. 3 shows an example of electrode arrangement of an electro-oculographic detector of a second embodiment (adhesive pad).

FIG. 3 shows an example of electrode arrangement of an electro-oculographic detector of a second embodiment (adhesive pad). Electro-oculographic (FOG) technology is expected to be used as communication means for heavily disabled persons such as amyotrophic lateral sclerosis (ALS) patients and hemiplegia patients by using their remaining functions (eye movements and blinking, for example). In such a use, adhesive pads are used as EOG electrodes as in electrocardiographic, electromyographic, and electroencephalographic measurements. FIG. 3 shows an ideal electrode arrangement when acquiring an electro-oculograph with adhesive pads.

In the example of FIG. 3, Ch1 detection electrodes (151*a* and 151*c*) are provided with the right eye side and Ch2 detection electrodes are not provided with the left eye side. Generally, both eyes are moved in the same direction in eye movements for the sake of communication, and thus, the detection of the vertical eye movements can be performed with Ch1 only. In the embodiment of FIG. 3, detection electrodes (151*b* and 152*b*) for horizontal eye movements are provided to avoid the predetermined left area (AXL) and predetermined right area (AXR).

Figure 4:
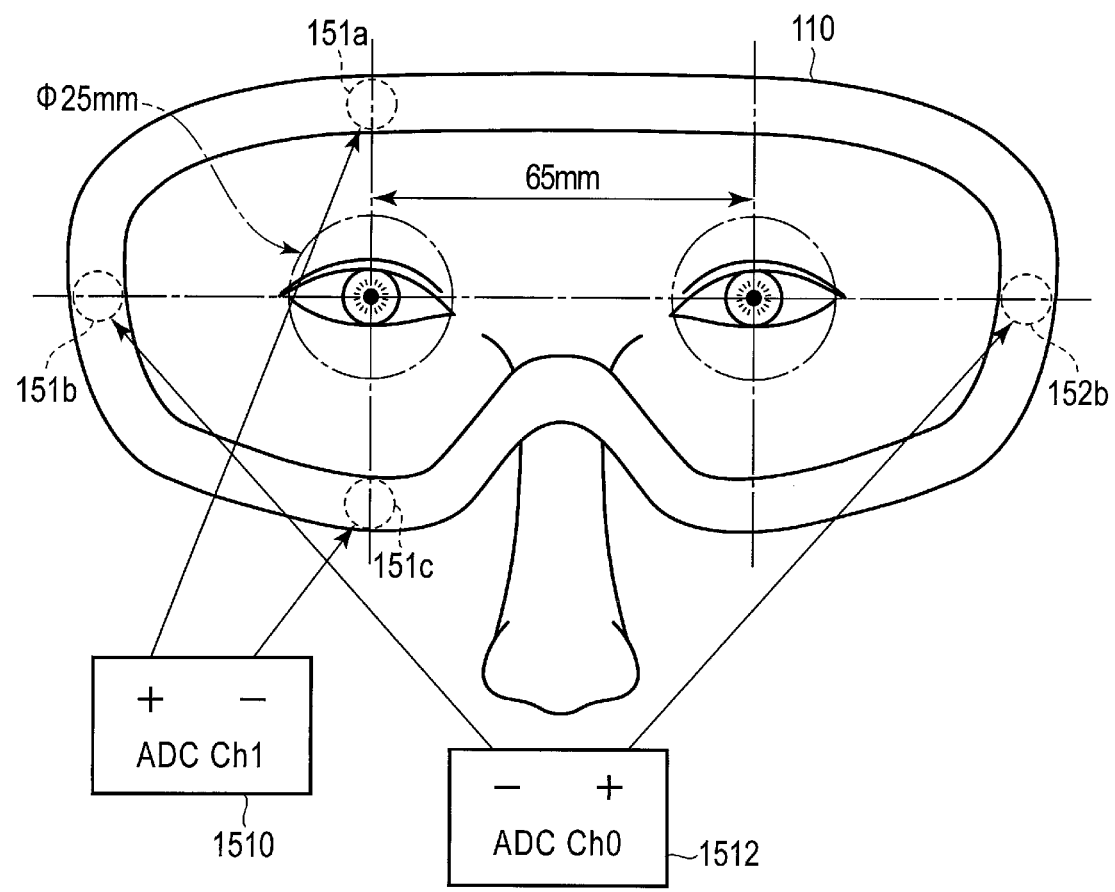
FIG. 4 shows a first example of electrode implementation of an electro-oculographic detector of a third embodiment (goggles).

FIG. 4 shows a first example of electrode implementation of an electro-oculographic detector of a third embodiment (goggles). If the adhesive pad type is not adopted, the electrode arrangement of FIG. 3 can be provided with the cushion on the frame 110 of the goggles as in FIG. 4. In this example, Ch0 detection electrodes (151*b* and 152*b*) are arranged on the horizontal line connecting the centers of both eyes.

FIG. 5 shows a second example of electrode implementation of the electro-oculographic detector of the third embodiment (goggles). The example of FIG. 5 differs from the example of FIG. 4 in a point that Ch0 detection electrodes (151*b* and 152*b*) are provided below the horizontal line connecting the centers of both eyes.

If goggles are put on the face of a user who is wearing vision correcting glasses, the temples of the glasses (in the proximity of the left and right hinges) may possibly interfere with Ch0 detection electrodes (151*b* and 152*b*) in the first example of the electrode implementation of FIG. 4. To avoid such interference, Ch0 detection electrodes (151*b* and 152*b*) are offset vertically in the second example of the electrode implementation of FIG. 5.

FIG. 6 shows an example of electrode arrangement and electrode implementation of an electro-oculographic detector of a fourth embodiment (goggles). In the example, channel 3 detection electrodes (151*d* and 152*d*) similar to Ch0 detection electrodes (151*b* and 152*b*) of FIG. 5 are arranged above the horizontal line connecting the centers of both eyes (that is, two pairs of horizontal detection electrodes are arranged). Furthermore, Ch2 detection electrodes (152a and 152c) similar to Ch1 detection electrodes (151a and 151c) of FIG. 5 are provided with the left eye side (that is, two pairs of vertical detection electrodes are arranged). That is, the electrode arrangement of FIG. 4 or 5 is doubled in the horizontal and vertical directions in the example of FIG. 6 to increase the credibility of the detection.

In the example of FIG. 6, horizontal and vertical signals can be acquired in a redundant manner even if any of EOG electrodes temporarily loses a contact with the skin by a body movement or a face movement. That is, even if a contact between the electrodes of any one of the two electrode pairs and the skin temporarily fails, the failure pair can be detected and the process can be continued using the detection signals obtained from the working pair.

A failure can be detected by, for example, determining whether a change in detection signals is within a range of biogenic signals which are ordinarily detectable. Whether or not a change in detection signals is within a range of biogenic signals can be determined by, for example, checking if a differential amount of the detection signals exceeds a predetermined value. Here, the size of the differential amount may include two types. If a first differential amount is great, an amplitude value of a predetermined time is great (a change of the signals is greater than an eye movement). If a second differential amount is great, an inclination of a signal level is great (a change of the signals is faster than an eye movement) regardless of a size of an amplitude. A sample rate of ADC can be suppressed in the detection of the first differential amount as compared to the detection of the second differential amount. Therefore, the detection of the first differential amount is easier from the implementation standpoint.

Note that the frame 110 with the electro-oculographic detection electrodes as in FIGS. 2, and 4 to 6 can be provided with other devices. For example, although this is not depicted, the frame 110 with electro-oculographic detection electrodes can be provided with an eyepiece of a telescope in an observatory. Thereby, a user of the telescope under the control of a computer can instruct a zoom-in/zoom-out operation of the telescope through the computer by an ocular action (eye-motion) of the user (for example, winking of either eye).

Alternatively, although this is not depicted, the frame 110 with the electro-oculographic detection electrodes (AR display type) can be provided with an eyepiece of a microscope. Thereby, a user of the microscope can make instructions to the microscope such that a target of inspection at a point of the sight with digital data can be marked by an ocular action (for example, blinking several times), or such that a position to be marked can be moved by a different ocular action (for example, vertical and horizontal eye movements), or such that image data of a part of the inspection target can be extracted by a different ocular action (for example, brief closing of the eyes).

Alternatively, although this is not depicted, the frame 110 with the electro-oculographic detection electrodes can be provided with an eyepiece at a lower side of an industrial periscope (such as a car inspection periscope of a bullet train). When a roof of a car is checked by such a periscope from the ground position, a direction and zoom of an objective lens at an upper side of the periscope can be controlled by ocular actions (eye-motion) of an inspection operator using the eyepiece of the periscope.

FIG. 7 shows an example of electrode arrangement of an electro-oculographic detector of a fifth embodiment (glasses) (which is different from the electrode arrangements shown in FIGS. 1 to 6).

When shapes of face and nose of a user are ignored, four EOG electrodes should be arranged as follows to avoid the mixture of signal amplitude and horizontal and vertical signals during the electro-oculographic measurement.

A vertical positional relationship of electrodes should be made such that upper and lower electrodes (151a and 152a, and 151b and 152b) are arranged with the horizontal line connecting the centers of both eyes interposed therebetween;

a horizontal positional relationship of electrodes should be made such that pairs of electrodes arranged side-by-side (a pair of 151a and 152a for Ch1 and a pair of 152a and 152b for Ch2) are aligned vertically; and Ch0 electrodes horizontally (151b and 152b) should be arranged to have a maximum gap therebetween while avoiding the predetermined right and left areas (AXL and AXR as in FIG. 1).

Figure 8:
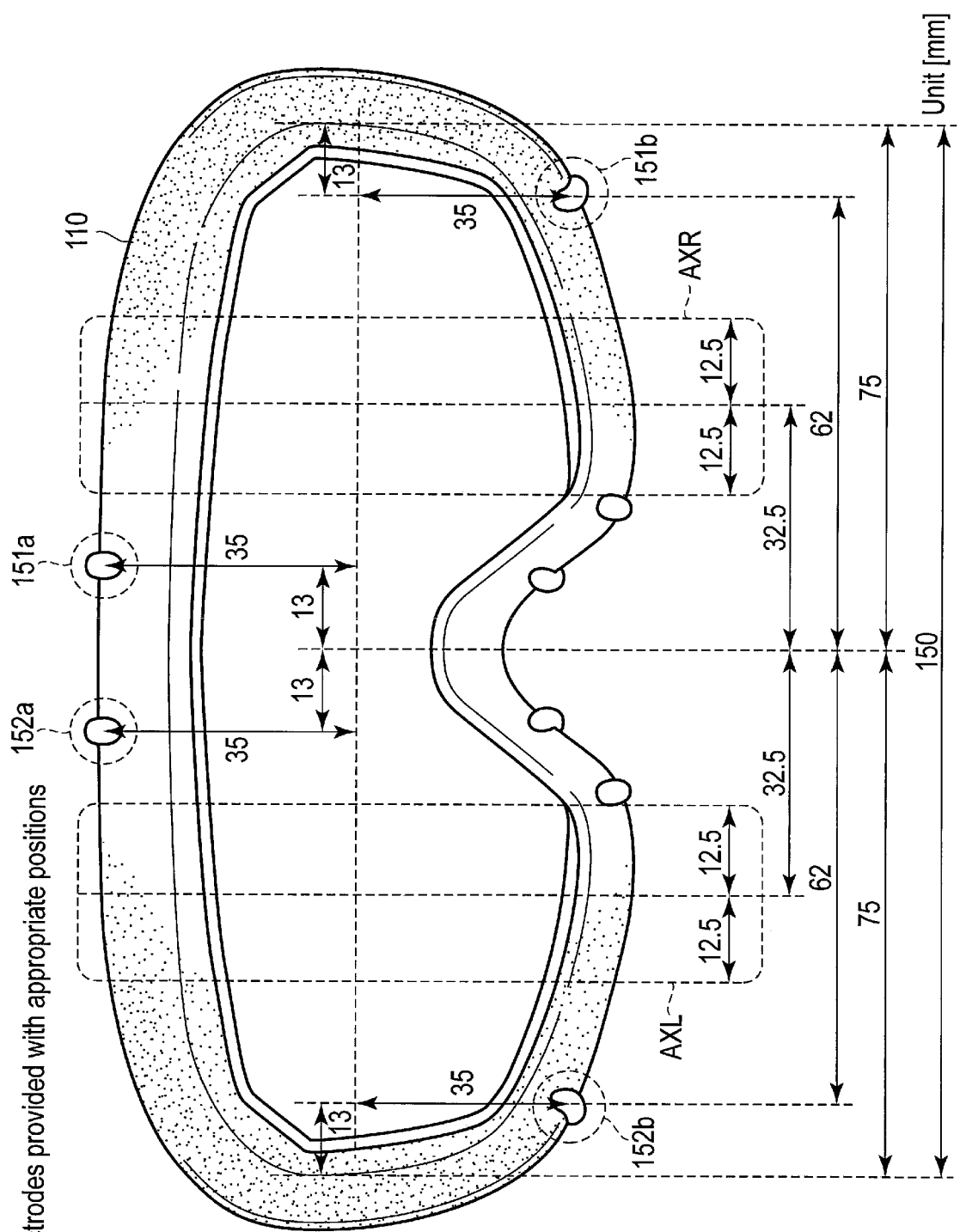
FIG. 8 shows an example of dimensions of optical head-mounted display goggles with electro-oculographic detection electrodes arranged with appropriate positions (and is viewed from the face of a user).

FIG. 8 shows an example of dimensions of goggles with electro-oculographic detection electrodes arranged with appropriate positions (which is referred to as Evaluation 1). FIG. 8 is a view being viewed from the face of a user. In this dimensional example, two EOG electrodes (152a and 152b) in the left eye side and two EOG electrodes (151a and 151b) in the right eye side are arranged symmetrically with respect to a vertical line passing the middle point of the line connecting the centers of both eyes. The vertical line passes the center of the frame 110 and corresponds to, for example, the nasal crest (or nose line) of the user.

Furthermore, upper two EOG electrodes (151a and 152a) are arranged 35 mm above the line connecting the centers of both eyes and lower two EOG electrodes (151b and 152b) are arranged 35 mm below the line connecting the centers of both eyes. The upper two EOG electrodes (151a and 152a) are arranged in the right and left of the vertical line passing the center of the frame 110 with an approximately 13 mm gap from the vertical line. The lower two EOG electrodes (151b and 152b) are arranged in the right and left of the vertical line passing the center of the frame 110 with an approximately 62 mm gap from the vertical line.

In the example of FIG. 8, two electrodes above the line connecting the centers of both eyes (151a and 152a) and two electrodes below the line connecting the centers of both eyes (151b and 152b) are arranged to avoid the predetermined left area (AXL) and the predetermined right area (AXR). Here, the predetermined left area (AXL) includes an inflection point where the detection polarity of the electro-oculograph differs in the right and left of a vertical line passing the center of the left eye (P1 of FIG. 2) (and consequently the signal phase of Ch2 is reversed). In the example of FIG. 8, the predetermined left area (AXL) is 12.5 mm right and left from the vertical line passing the center of the left eye where the diameter of the left eye is 25 mm. Furthermore, the predetermined right eye area (AXR) includes an inflection point where the detection polarity of the electro-oculograph differs in the right and left of a vertical line passing the center of the right eye (P2 of FIG. 2) (and consequently the signal phase of Ch1 is reversed). In the example of FIG. 8, the predetermined right area (AXR) is 12.5 mm right and left from the vertical line passing the center of the right eye where the diameter of the right eye is 25 mm. The vertical dimension of each of the predetermined right and left areas (AXR and AXL) are optional and should arbitrarily be determined corresponding to the size of the frame 110 to which EOG electrodes are implemented.

Figure 9:
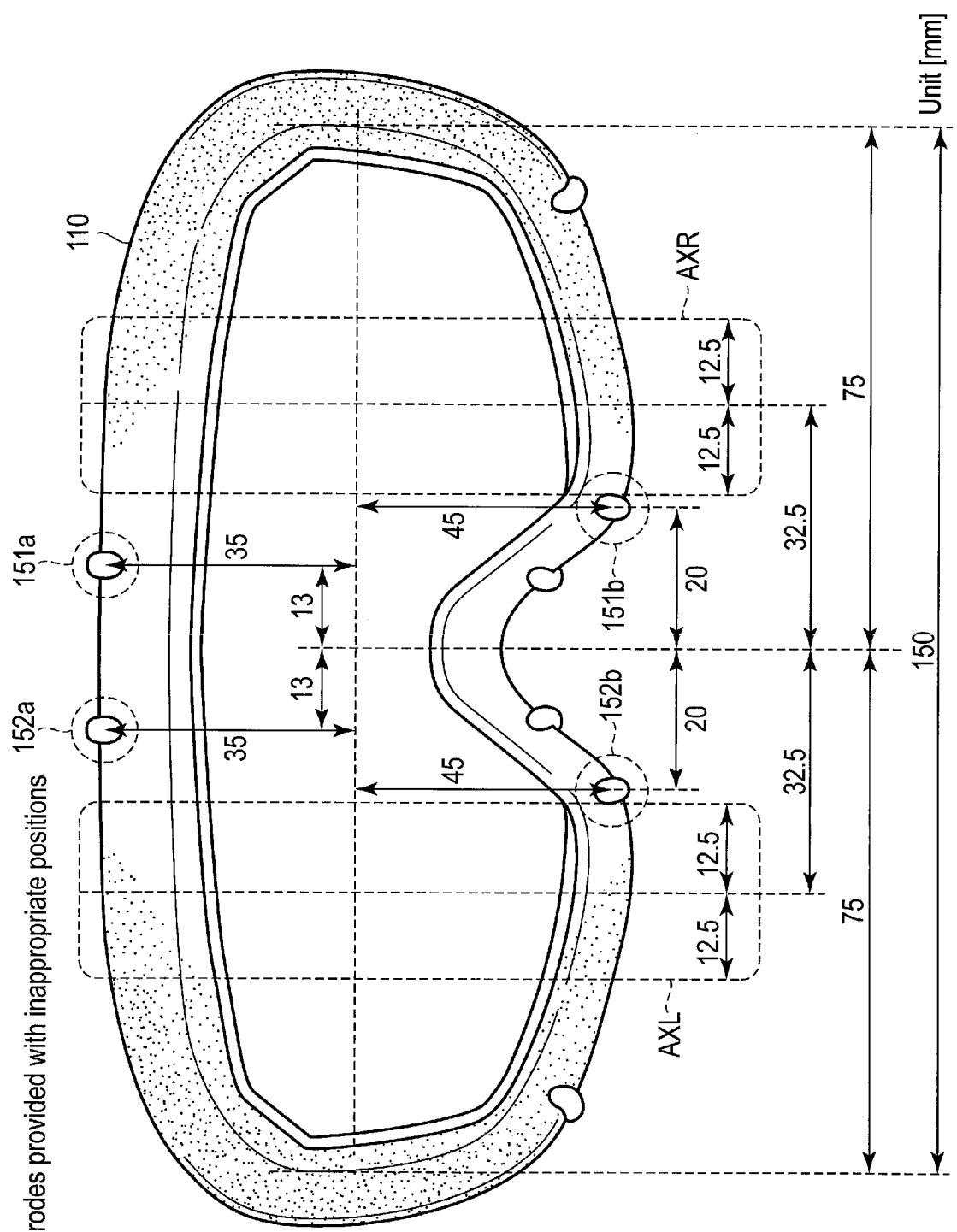
FIG. 9 shows an example of dimensions of a optical head-mounted display goggles with electro-oculographic detection electrodes of which Ch0 signal detection electrodes are arranged inappropriately (which is referred to as Evaluation 2)

FIG. 9 shows an example of dimensions of goggles with electro-oculographic detection electrodes in which Ch0 signal detection electrodes are arranged inappropriately (which is referred to as Evaluation 2), and FIG. 9 is a view being viewed from the face of a user. In this dimensional example, two EOG electrodes (152a and 152b) in the left eye side and two EOG electrodes (151a and 151b) in the right eye side are arranged symmetrically with respect to a vertical line passing the middle point of the line connecting the centers of both eyes (as in FIG. 8).

Furthermore, upper two EOG electrodes (151a and 152a) are arranged 35 mm above the line connecting the centers of both eyes and lower two EOG electrodes (151b and 152b) are arranged 35 mm below the line connecting the centers of both eyes (as in FIG. 8). The upper two EOG electrodes (151a and 152a) are arranged in the right and left of the vertical line passing the center of the frame 110 with an approximately 13 mm gap from the vertical line (as in FIG. 8).

However, the lower two EOG electrodes (151b and 152b) are arranged in the right and left of the vertical line passing the center of the frame 110 with an approximately 20 mm gap from the vertical line (unlike FIG. 8). That is, the lower two EOG electrodes (151b and 152b) are arranged to slightly touch the predetermined left area (AXL) and the predetermined right area (AXR) (unlike FIG. 8).

Figure 10:
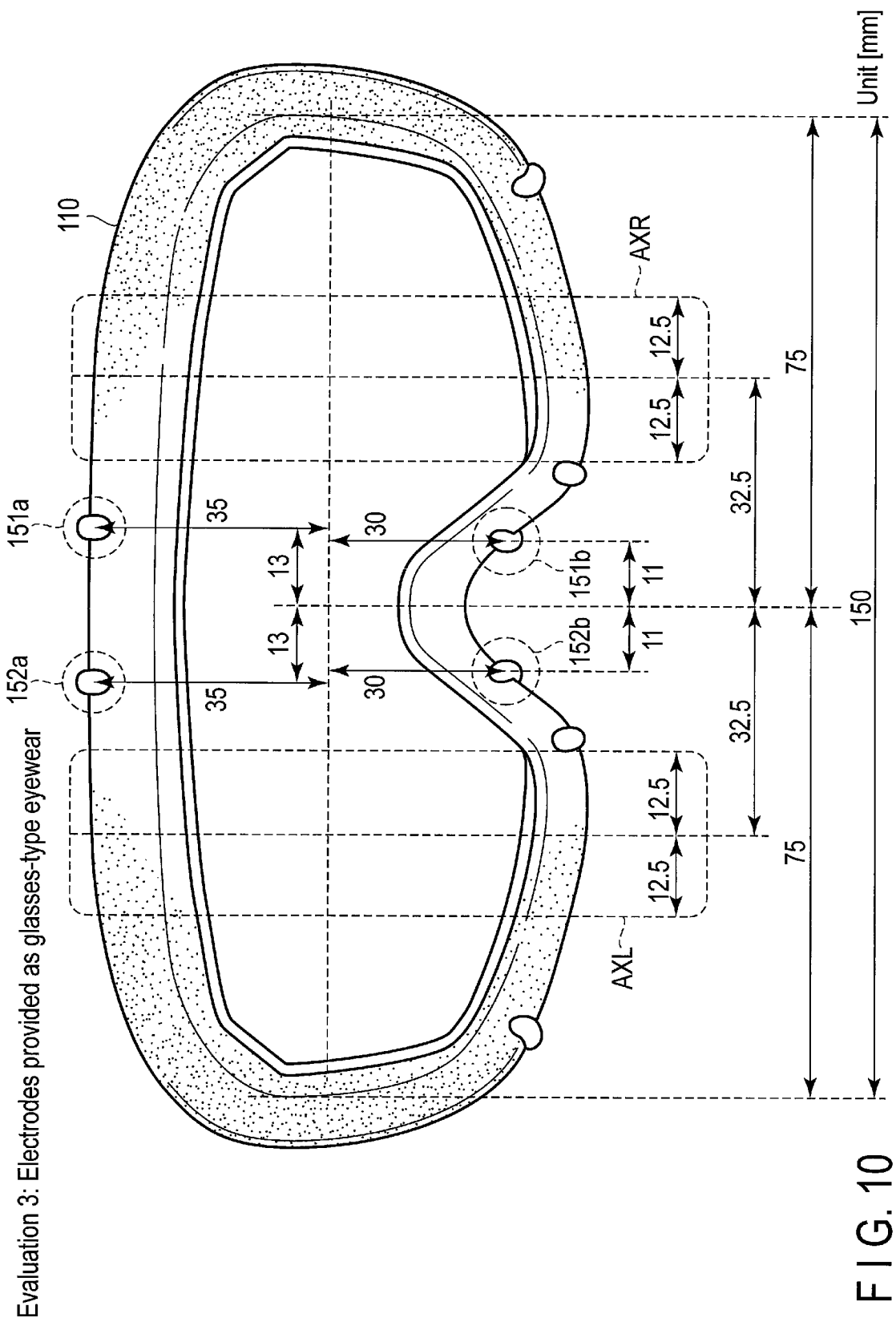
FIG. 10 shows an example of dimensions of optical head-mounted display goggles with electro-oculographic detection electrodes arranged in a not most appropriate but acceptable manner.

FIG. 10 shows an example of dimensions of goggles with electro-oculographic detection electrodes arranged in a not most appropriate but acceptable manner (which is referred to as Evaluation 3), and FIG. 10 is a view being viewed from the face of a user. In this dimensional example, two EOG electrodes (152a and 152b) in the left eye side and two EOG electrodes (151a and 151b) in the right eye side are arranged symmetrically with respect to a vertical line passing the middle point of the line connecting the centers of both eyes (as in FIG. 8).

Furthermore, upper two EOG electrodes (151a and 152a) are arranged 35 mm above the line connecting the centers of both eyes and lower two EOG electrodes (151b and 152b) are arranged 35 mm below the line connecting the centers of both eyes (as in FIG. 8). The upper two EOG electrodes (151a and 152a) are arranged in the right and left of the vertical line passing the center of the frame 110 with an approximately 13 mm gap from the vertical line (as in FIG. 8).

However, the lower two EOG electrodes (151b and 152b) are arranged in the right and left of the vertical line passing the center of the frame 110 with an approximately 11 mm gap from the vertical line (unlike FIGS. 8 and 9). That is, the lower two electrodes (151b and 152b) are arranged to avoid the predetermined left area (AXL) and the predetermined right area (AXR) in a manner different from that of FIG. 8.

FIG. 11 shows an example of waveforms of an electro-oculograph (EOG) obtained through various ocular actions (blinking, closing of the eyes, and vertical and horizontal eye movements). The same ocular actions (eye-motion) are measured with respect to Evaluations 1 to 3 of FIGS. 8 to 10, and FIG. 11 shows a result of waveforms measured from the case of FIG. 8 (Evaluation 1). In the electrode arrangement of FIG. 8 (and FIG. 2), electrodes at right and left sides are arranged diagonally and right and left pairs of electrodes are arranged symmetrically with respect to the bridge of the user's nose.

In FIG. 11, the vertical axis (Y-axis) shows signal level (amplitude values) and the horizontal axis (X-axis) shows time. The Y-axis show sample values measured where an ADC having an operation voltage of 3.3 V and a resolution of 24 bits is used. Therein, the weight of the detection signal level is 3.3 V/$2^{24}$=196.695 nV≈200 nV. Thus, each gap of the vertical axis (20000) in FIG. 11 represents 20000× 196.695 nV≈4 mV. Furthermore, the X-axis indicates the number of samples of 256 fs, and when a difference between two adjacent values in the X-axis is divided by 256, how many seconds have passed can be recognized.

In FIG. 11, period TX10 shows an example of detection signal waveforms of Ch0 to Ch2 measured for one to three blinks and one closing of the eyes for one second (with the electrode arrangement of Evaluation 1 of FIG. 8), and period TX40 shows an example of detection signal waveforms of Ch0 to Ch2 when the same ocular actions (eye-motion) are performed (with the electrode arrangement of Evaluation 1 of FIG. 8). The examples of the waveforms in periods TX10 and TX40 show that the same detection signal waveforms can be obtained from the same ocular actions even with different measurement times.

During each of periods TX10 and TX40, the detection signal waveform of Ch0 does not substantially change in response to rapid blinks each lasting a fraction of a second. However, the detection signal waveforms of Ch1 and Ch2 change clearly in response to the number of blinks. The detection signal waveform of Ch0 changes slightly in response to closing of the eyes which takes longer than a blink; however, the detection signal waveforms of Ch1 and Ch2 change more clearly than that of Ch0.

In FIG. 11, period TX20 shows an example of detection signal waveforms of Ch0 to Ch2 measured when the eyes directed ahead move leftward, stay still for approximately one second, and then return to their original position, and measured when the eyes directed ahead move rightward, stay still for approximately one second, and then return to their original position (with the electrode arrangement of Evaluation 1 of FIG. 8). Significantly, with the electrode arrangement of Evaluation 1 of FIG. 8, the phase of detection signal is reversed between Ch1 and Ch2 in response to the horizontal eye movement and the amplitude of the detection signal of Ch0 becomes great.

In FIG. 11, period TX30 shows an example of detection signal waveforms of Ch0 to Ch2 measured when the eyes directed ahead move upward, stay still for approximately one second, and then return to their original position, and measured when the eyes directed ahead move downward, stay still for approximately one second, and then return to their original position (with the electrode arrangement of Evaluation 1 of FIG. 8). During the vertical eye movement, the waveform of Ch0 does not change substantially while the waveforms of Ch1 and Ch2 change similarly.

As is evident from the example of waveforms in FIG. 11, the number of blinks, discrimination between blinking and closing of the eyes, discrimination of horizontal eye movement, and discrimination of vertical eye movement can be acknowledged based on detection signal waveforms of Ch0 to Ch2.

Types of eye movement and ranges of eye movement related to the eye movement detection are, for example, as follows.

<Types of Eye Movement>

(01) Compensative Eye Movement

Involuntary eye movement developed for stabilizing an external image on the retina regardless of movements of the head or body.

(02) Voluntary Eye Movement

Eye movement developed to set a target image to the center of the retina and controlled voluntarily.

(03) Impulsive Eye Movement (Saccade)

Eye movement made when a fixation is changed to see an object (easy to detect).

(04) Slide Eye Movement

Smooth eye movement made when tracking an object moving slowly (hard to detect).

<Movement Range of Eyes (of an Ordinary Adult)>

(11) Horizontal Directions

Left direction: 50° or less

Right direction: 50° or less

(12) Vertical Directions

Downward direction: 50° or less

Upward direction: 30° or less (The range of angles of the eyes voluntarily movable vertically is narrower in the upper direction. Because of the Bell phenomenon by which eyes rotate upward when the eyes are closed, the eye movement range vertically shifts to the upward direction when the eyes are closed.)

(13) Others (Eye Movements not Performed in Evaluations 1 to 3)

Angle of convergence: 20° or less

Figure 12:
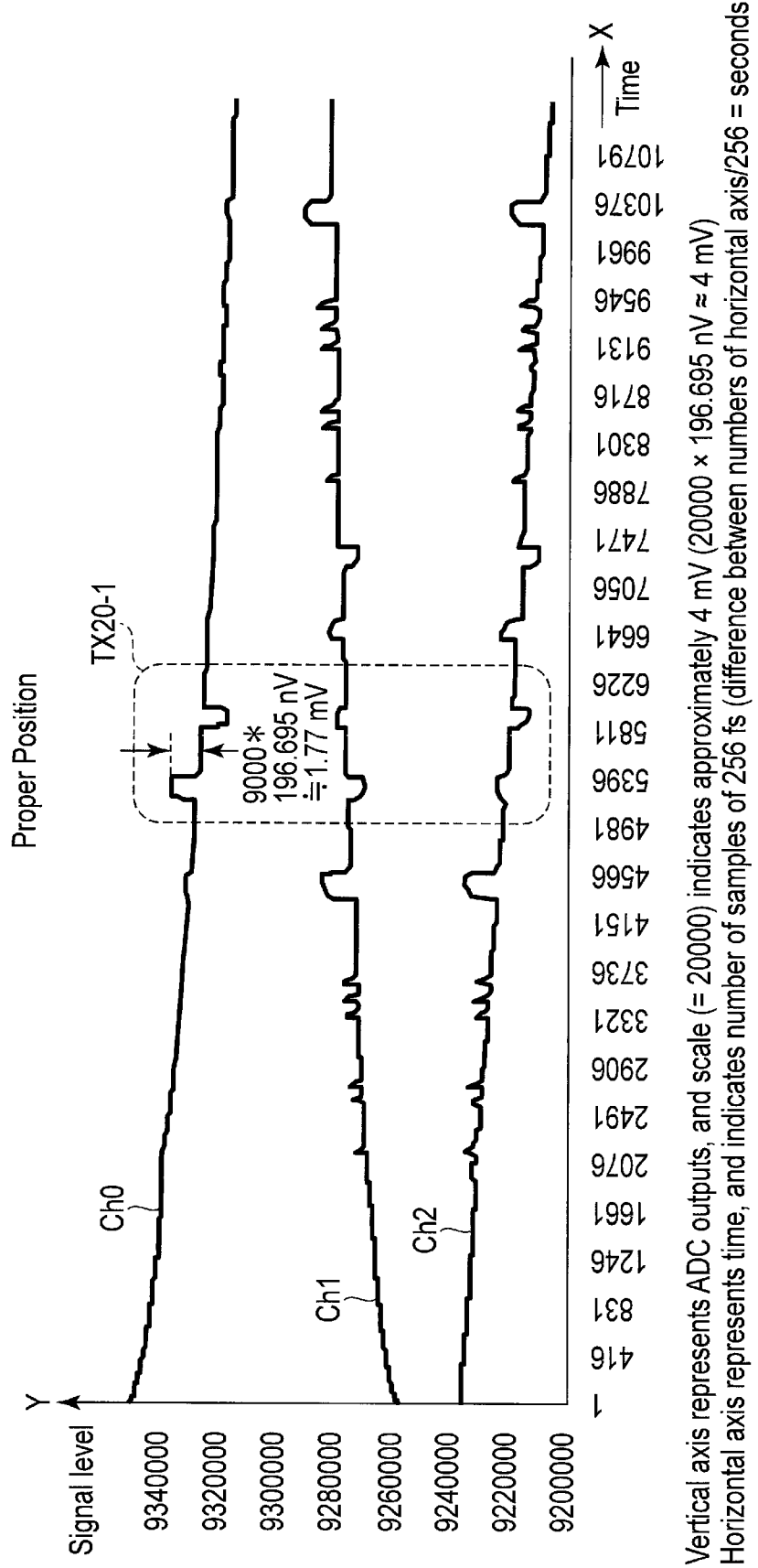
FIG. 12 shows an example of waveforms of an electro-oculograph obtained corresponding to various ocular actions (blinking, closing of the eyes, and horizontal and vertical eye movements) measured by optical head-mounted display goggles in which electro-oculographic detection electrodes are provided with appropriate positions therein.

FIG. 12 shows an example of waveforms of an electro-oculograph obtained corresponding to various ocular actions (blinking, closing of the eyes, and horizontal and vertical eye movements) measured by goggles in which electro-oculographic detection electrodes are provided with appropriate positions therein (that is, EOG waveforms measured in Evaluation 1). Although the values of X-axis of FIG. 12 are different from that of FIG. 11, the waveforms of these figures show a good affinity. In the example of Evaluation 1 (FIG. 8), a Ch0 signal of approximately 1.77 mV is detected in response to an eye movement horizontally (cf. period TX20-1 of FIG. 12).

Figure 13:
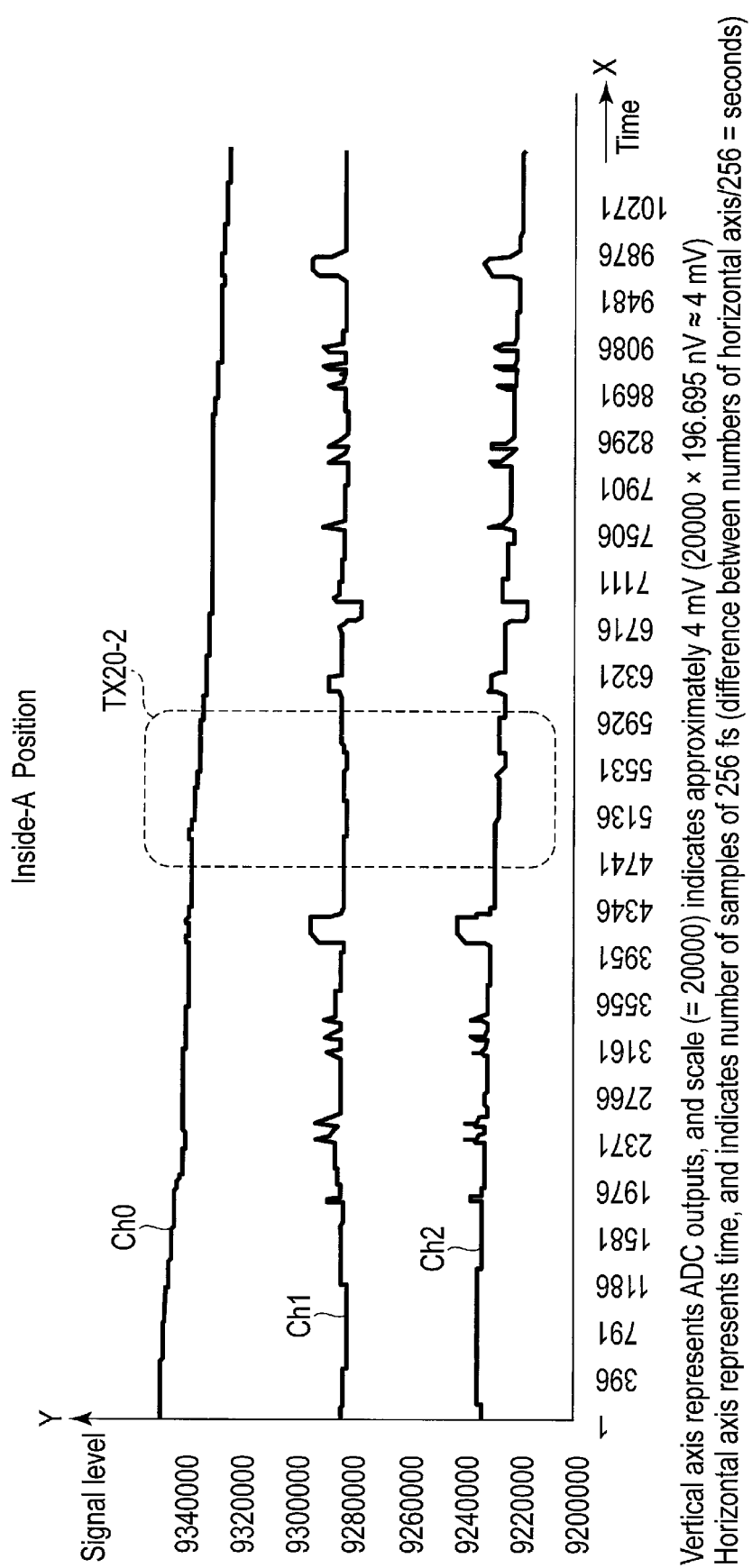
FIG. 13 shows an example of waveforms of an electro-oculograph obtained corresponding to various ocular actions (blinking, closing of the eyes, and horizontal and vertical eye movements) measured by optical head-mounted display goggles in which electro-oculographic detection electrodes for Ch0 signal detection are provided with inappropriate positions therein.

FIG. 13 shows an example of waveforms of an electro-oculograph obtained corresponding to various ocular actions (blinking, closing of the eyes, and horizontal and vertical eye movements) measured by goggles in which electro-oculographic detection electrodes for Ch0 signal detection are provided with inappropriate positions therein (that is, EOG waveforms measured in Evaluation 2). In the example of Evaluation 2 (FIG. 9), no signals from Ch0 to Ch2 are detected in response to an eye movement horizontally (cf. period TX20-2 of FIG. 13).

Figure 14:
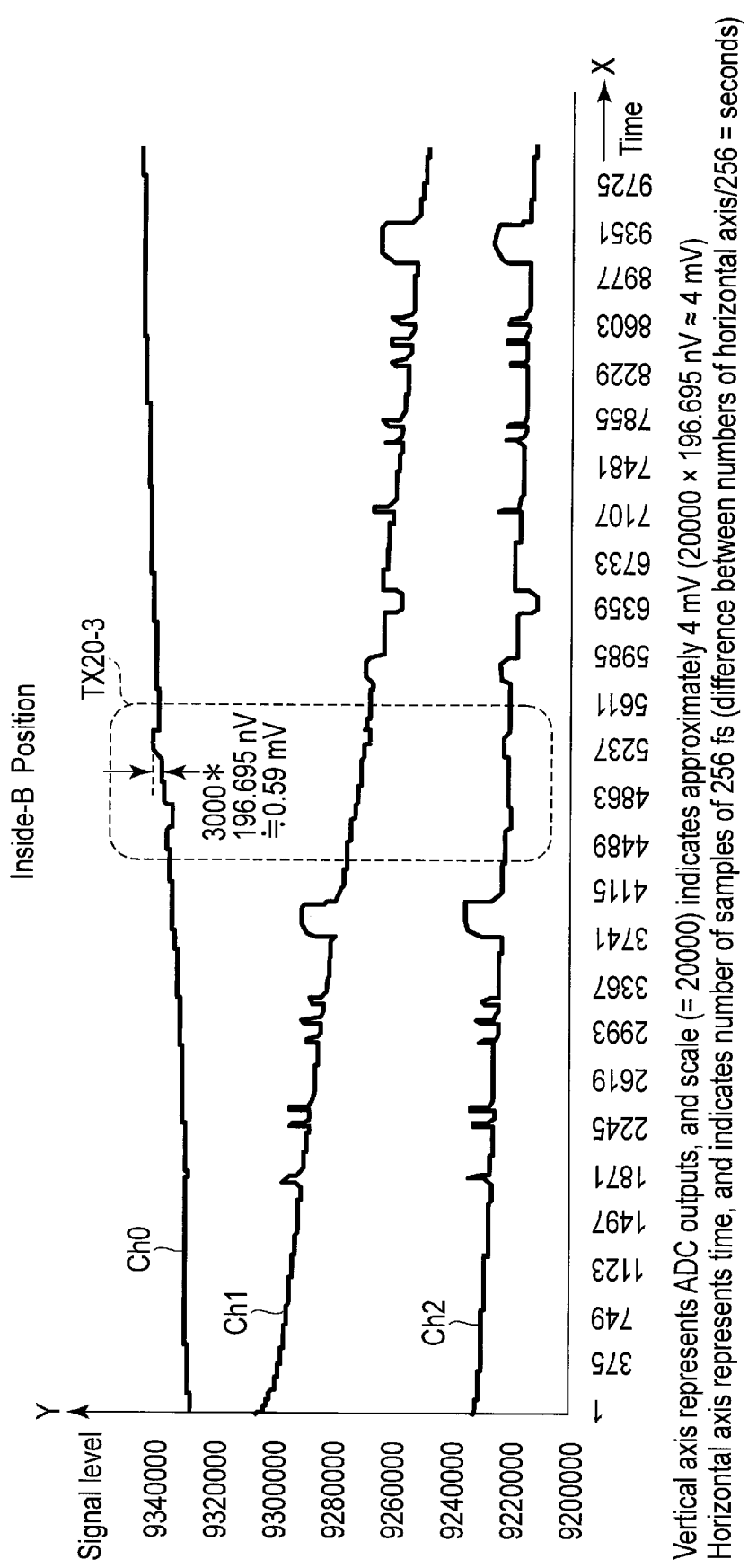
FIG. 14 shows an example of waveforms of an electro-oculograph obtained corresponding to various ocular actions (blinking, closing of the eyes, and horizontal and vertical eye movements) measured by optical head-mounted display goggles in which electro-oculographic detection electrodes are provided with not-appropriate but acceptable positions therein.

FIG. 14 shows an example of waveforms of an electro-oculograph obtained corresponding to various ocular actions (blinking, closing of the eyes, and horizontal and vertical eye movements) measured by goggles in which electro-oculographic detection electrodes are provided with not-appropriate but acceptable positions therein (that is, EOG waveforms measured in Evaluation 3). In the example of Evaluation 3 (FIG. 10), a Ch0 signal of 0.59 mV is detected in response to an eye movement horizontally (cf. period TX20-3 of FIG. 14). This value is one third of that of Evaluation 1 (FIG. 8) and is easily affected by noise. A simple rightward or leftward eye movement may be detected by Evaluation 3 (FIG. 10); however, a highly accurate detection such as measuring a specific degree of a rightward (or leftward) eye movement should be performed in Evaluation 1 (FIG. 8) for the sake of better appropriateness.

<Detection of Wink>

Movement of the human eye is made by cooperation of an eyelid and muscle, and when the eye is closed, the eyeball turns upward. Thus, only the eyeball winking turns upward.

In Ch1/Ch2, the detection signal amplitude of electrodes closer to the winking eye becomes relatively large; however, a winking detection by Ch1/Ch2 is relatively difficult (since detection signal amplitudes of both eyes cannot be equal in winking, a different of a change ratio of the amplitudes or the like must be checked).

Alternatively, in Ch0, a signal change by winking appears in a positive/negative electrode, and phases of signals of right and left eyes are reversed. Thus, winking of right or left eye can be easily detected distinguishably.

Figure 15:
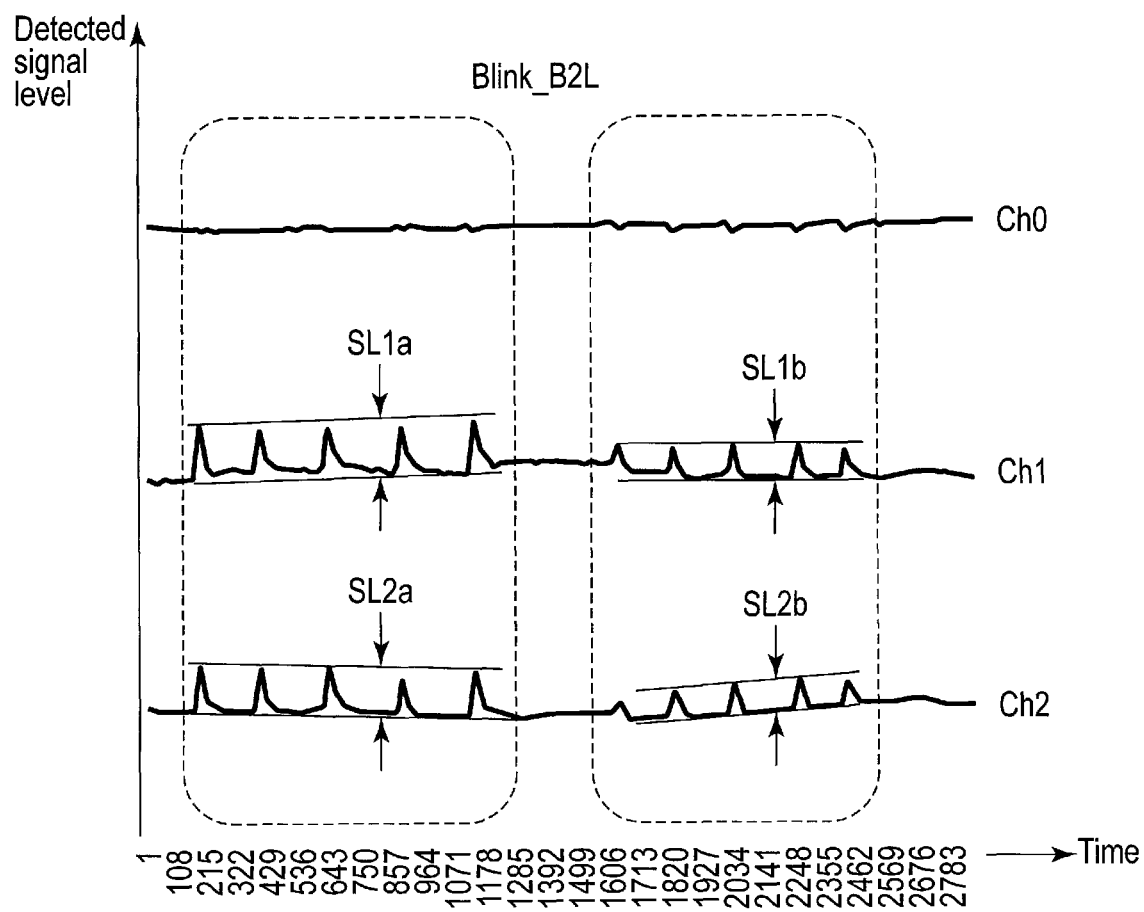
FIG. 15 shows an example of waveforms of an electro-oculograph obtained when the eyes directed ahead are blinked five times and the left eye winked five times (blinking of the left eye).

FIG. 15 shows an example of waveforms of an electro-oculograph obtained when the eyes directed ahead blink five times and the left eye winks five times (blinking of the left eye). The example of FIG. 15 corresponds to a case where Ch0 detection electrodes are offset below the horizontal line connecting the centers of both eyes as in FIGS. 1 and 7.

If the electrodes of ADC 1512 of Ch0 are positioned below the horizontal line connecting the centers of both eyes as in FIGS. 1 and 7, a negative direction potential change appears in both positive and negative inputs of ADC 1512 in response to blinking of both eyes. Given that the potential changes (amount and direction) of both the positive and negative inputs are substantially the same, the changes are substantially canceled, and the signal levels output from ADC 1512 of Ch0 become substantially the same (cf. Ch0 level within the dotted-line circle in the left side of FIG. 15). On the other hand, a potential change in the negative input of ADC 1512 is hardly recognizable but a relatively large negative direction potential change appears in the positive input of ADC 1512 in response to one eye (left eye) blinking. That is, the cancel in potential changes between the positive and negative inputs of ADC 1512 becomes small, and the signal level output from ADC 1512 of Ch0 shows small pulses in the negative direction (small waves of signal level) (cf. Ch0 level within the dotted-line circle in the right side of FIG. 15). From the polarity of the small waves (pulses in the negative direction) of the signal level, left-eye winking can be detected (this is an example of left-eye winking detection, which uses Ch0).

In the example of FIG. 6, electrodes of ADC 1514 of channel 3 are positioned above the horizontal line connecting the centers of both eyes. Because of the arrangement, a positive direction potential change appears in both the positive and negative inputs of ADC 1514 in response to blinking of both eyes. Given that the potential changes (amount and direction) of both the positive and negative inputs are substantially the same, the changes are substantially canceled, and the signal levels output from ADC 1514 of channel 3 become substantially the same. On the other hand, a potential change in the negative input of ADC 1514 is hardly recognizable but a relatively large positive direction potential change appears in the positive input of ADC 1514. That is, the cancel in potential changes between the positive and negative inputs of ADC 1514 becomes small, and the signal level output from ADC 1514 of channel 3 shows small pulses in the positive direction (small waves of signal level which are not shown). From the polarity of the small waves (pulses in the positive direction) of the signal level, left-eye winking can be detected (this is another example of left-eye winking detection, which uses channel 3).

If the potential changes between the positive and negative inputs of ADC 1512 are not even because of an unbalanced shape of the face of a user or of a skin condition, a calibration should be performed when the user wears an eyewear 100 such that the output of ADC of Ch0 is set to maximum in response to blinking of both eyes (such that the cancel amount between the positive and negative input components becomes maximum).

Furthermore, if a peak ratio SL1a/SL2a of detection signals Ch1/Ch2 measured in response to blinking of both eyes is given as a reference, a peak ratio SL1b/SL2b in response to a left-eye wink changes (SL1b/SL2b is not equal to SL1a/SL2a). Using this mechanism, a left wink can be detected.

FIG. 16 shows an example of waveforms of an electro-oculograph obtained when the eyes directed ahead blink five times and the right eye winks five times (blinking of the right eye). The example of FIG. 16 corresponds to a case where Ch0 detection electrodes are offset below the horizontal line connecting the centers of both eyes as in FIGS. 1 and 7.

As explained above, if the electrodes of ADC 1512 are positioned below the horizontal line connecting the centers of both eyes as in FIGS. 1 and 7, a negative direction potential change appears in both positive and negative inputs of ADC 1512 in response to blinking of both eyes. However, similar potential changes in the positive and negative inputs are substantially canceled, and the signal levels output from ADC 1512 of Ch0 become substantially the same (cf. Ch0 level within the dotted-line circle in the left side of FIG. 16). On the other hand, a potential change in the positive input of ADC 1512 is hardly recognizable but a relatively large negative direction potential change appears in the positive input of ADC 1512 in response to one eye (right eye) blinking. That is, the cancel in potential changes between the positive and negative inputs of ADC 1512 becomes small, and the signal level output from ADC 1512 of Ch0 shows small pulses in the positive direction (small waves of signal level) (cf. Ch0 level within the dotted-line circle in the right side of FIG. 16). From the polarity of the small waves (pulses in the positive direction) of the signal level, right-eye winking can be detected (this is an example of right-eye winking detection, which uses Ch0).

Furthermore, if a peak ratio SR1a/SR2a of detection signals Ch1/Ch2 measured in response to blinking of both eyes is given as a reference, a peak ratio SR1b/SR2b in response to a right-eye wink changes (SR1b/SR2b is not equal to SR1a/SR2a). Furthermore, a peak ratio SL1b/SL2b measured in response to a left wink is different from a peak ratio SR1b/SR2b measured in response to a right wink (a degree of difference can be confirmed in an experiment). Using this mechanism, a left wink and a right wink can be detected distinguishably (an example of right and left wink detections, which uses Ch1 and Ch2).

In the example of FIG. 6, electrodes of ADC 1514 of channel 3 are positioned above the horizontal line connecting the centers of both eyes. Because of the arrangement, a positive direction potential change appears in both the positive and negative inputs of ADC 1514 in response to blinking of both eyes. Given that the potential changes (amount and direction) of both the positive and negative inputs are substantially the same, the changes are substantially canceled, and the signal levels output from ADC 1514 of channel 3 become substantially the same. On the other hand, a potential change in the positive input of ADC 1514 is hardly recognizable but a relatively large positive direction potential change appears in the negative input of ADC 1514. That is, the cancel in potential changes between the positive and negative inputs of ADC 1514 becomes small, and the signal level output from ADC 1514 of channel 3 shows small pulses in the negative direction (small waves of signal level which are not shown). From the polarity of the small waves (pulses in the negative direction) of the signal level, right-eye winking can be detected (this is another example of right-eye winking detection, which uses channel 3).

In the example of FIG. 6, a detection of a left wink can be performed using logical AND of a detection result of Ch0 and channel 3 or logical OR of a detection result of Ch0 and channel 3. Specifically, in the detection using logical AND, a left wink is acknowledged only when a negative direction pulse is detected in Ch0 and a positive direction pulse is detected in channel 3 (a possibility of misjudgment caused by irregular noises becomes low). In the detection using logical OR, a left wink is acknowledged when a negative direction pulse is detected in Ch0, or when a positive direction pulse is detected in channel 3 (a possibility of misjudgment caused by irregular noises becomes relatively high but the wink detection sensitivity increases).

Similarly, in the example of FIG. 6, a detection of a right wink can be performed using logical AND or logical OR of a detection result of Ch0 and channel 3. Specifically, in the detection using logical AND, a right wink is acknowledged only when a positive direction pulse is detected in Ch0 and a negative direction pulse is detected in channel 3. In the detection using logical OR, a right wink is acknowledged when a positive pulse is detected in Ch0, or when a negative direction pulse is detected in channel 3.

Note that, in the detection of right and left winks, the electrodes 151c and 152c of FIG. 6 may be connected to the negative and positive of ADC similar to Ch0 and/or the electrodes 151a and 152a of FIG. 6 may be connected to the negative and positive of ADC similar to channel 3 such that pulses shown in the right side of Ch0 waveforms in FIGS. 15 and 16 are detected.

Use of Ch0, channel 3, or Ch1/Ch2 for the detection of right and left winks should be determined arbitrarily by a designer of the device. A detection result of right and left winks using Ch0 to channel 3, etc. can be used as an operation command.

Furthermore, by using a timing of blink detection (with maximum detection level) in Ch1/Ch2 (to suppress affection of the noises), the polarity of small waves of the detection signal of Ch0 in the same timing can be detected.

Figure 17:
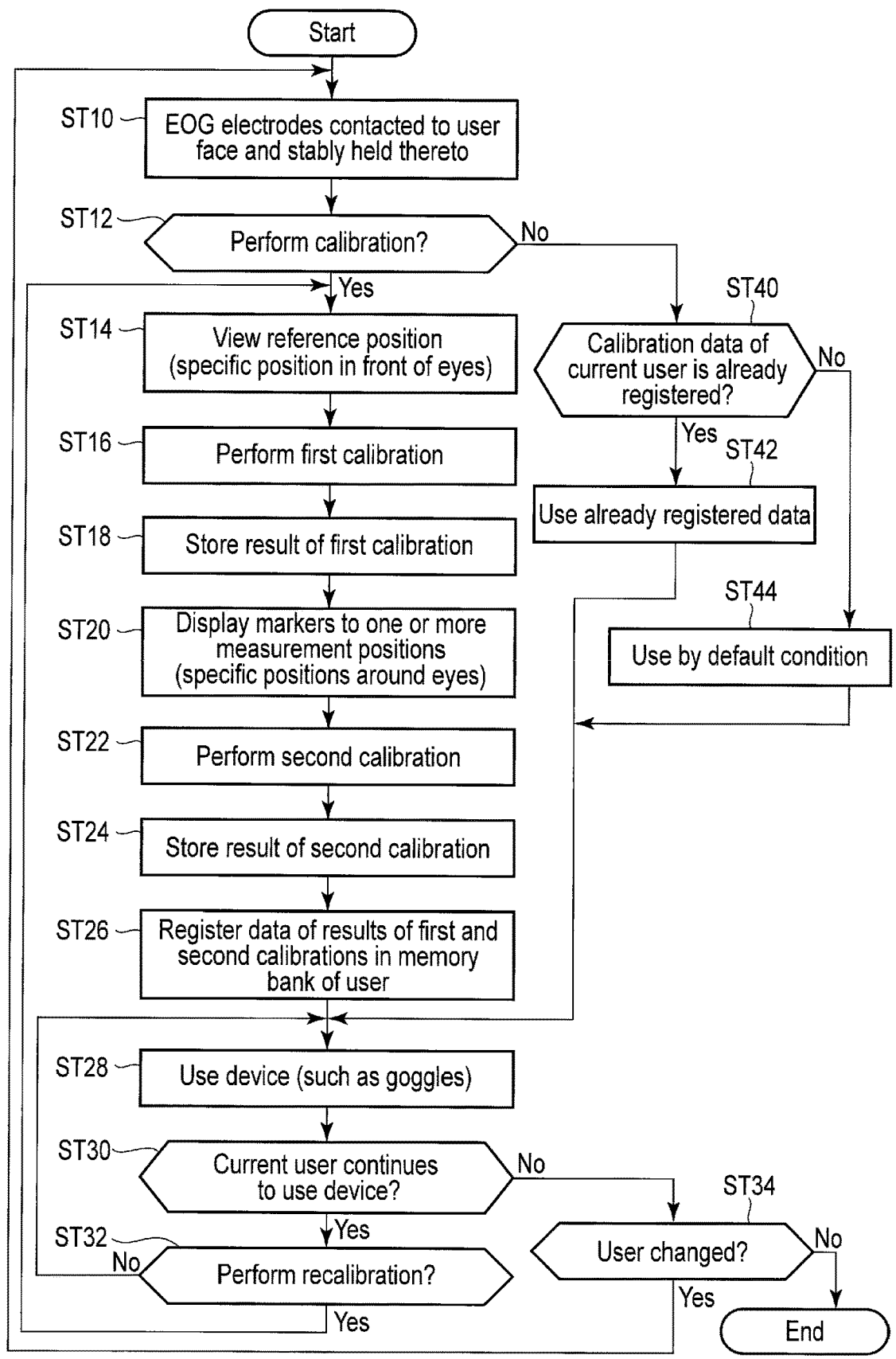
FIG. 17 shows a flowchart of an example of calibration performed by each user with respect to each embodiment.

FIG. 17 shows a flowchart of an example of calibration performed by each user with respect to each embodiment disclosed. In this example, calibration is performed using goggles with frame 110 including electro-oculographic detection electrodes/calibration markers as in FIG. 2.

When a user puts the goggles on such that the face firmly contacts the four electro-oculographic detection electrodes (EOG electrodes 151a, 151b, 152a, and 152b) on the frame 110, the user stably maintains the contact (ST10). The calibration is automatically initiated when the user puts the goggles on and maintains EOG electrodes in stable contact. Or, the calibration may be initiated by a manual operation by the user wearing the goggles. The calibration is performed by a data processor 11 in FIG. 19.

In this example, the calibration is divided into first calibration and second calibration (the divided of first calibration and second calibration is optional and a continued calibration process can be adopted).

The first calibration is performed to detect a state where the user stares ahead (a reference state which is unique to each user). The second calibration is performed using the state where the user stares ahead (a result of the first calibration) as a reference. The second calibration is performed to detect significances of various ocular actions (eye movement, blinking, closing of the eyes, winking, etc.) based on wave height, polarity, occurrence timing of detection signals from each channel (Ch0 to Ch2).

That is, when the calibration starts (Yes in ST12), the user looks straight at markers at reference positions P1 and P2 directly in front of the right and left eyes (ST14). While the user is looking straight at the markers at reference positions P1 and P2, the first calibration is performed (ST16). A result of the first calibration of ADC output level of each of Ch0, Ch1, and Ch2 is temporarily stored (ST18).

After the result of the first calibration is temporarily stored, one or more of four LED markers (M01, M02, M11, and M12) provided with predetermined positions of the frame 110 are lit (ST20). If only one LED marker is lit, that is a primary marker. If two or more LED markers are lit, one LED marker is set to a specific color (such as red) as a primary marker and the other LED markers are set to a different color (such as green) as not-primary markers (or secondary markers).

After the primary LED marker is lit, the second calibration is performed (ST22). In the second calibration, the user is prompted to see the LED light point of the primary marker to make an eye movement toward the primary marker. For example, when M01 which is one of the upper LED markers is the primary marker, both eyes of the user stop for a moment looking up. The internal condition of each ADC at that time (circuit gain before digitization and/or multiplication factor after digitization, etc.) is corrected such that the ADC output level of each Ch1 and Ch2 becomes a predetermined value. A result of the correction (ADC output level of each of Ch0 to Ch2 and data of the internal condition of each ADC measured when the output level is obtained) is temporarily stored as a temporary calibration result (result 1).

The primary marker is then switched to a lower LED marker M02, and both eyes of the user stop for a moment looking down. The internal condition of each ADC at that time (circuit gain before digitization and/or multiplication factor after digitization, etc.) is corrected such that the ADC output level of each Ch1 and Ch2 becomes a predetermined value. A result of the correction (ADC output level of each of Ch0 to Ch2 and data of the internal condition of each ADC measured when the output level is obtained) is temporarily stored as a temporary calibration result (result 2).

The primary marker is then switched to a right LED marker M11, and both eyes of the user stop for a moment looking right. The internal condition of each ADC at that time (circuit gain before digitization and/or multiplication factor after digitization, etc.) is corrected such that the ADC output level of each Ch1 and Ch2 becomes a predetermined value. A result of the correction (ADC output level of each of Ch0 to Ch2 and data of the internal condition of each ADC measured when the output level is obtained) is temporarily stored as a temporary calibration result (result 3).

The primary marker is then switched to a left LED marker M12, and both eyes of the user stop for a moment looking left. The internal condition of each ADC at that time (circuit gain before digitization and/or multiplication factor after digitization, etc.) is corrected such that the ADC output level of each Ch1 and Ch2 becomes a predetermined value. A result of the correction (ADC output level of each of Ch0 to Ch2 and data of the internal condition of each ADC measured when the output level is obtained) is temporarily stored as a temporary calibration result (result 4).

The primary marker is switched sequentially as above, and temporary calibration results (results 1 to 4) are gathered and temporarily stored as a second calibration result (ST24).

The temporarily stored first and second calibration results are registered in a memory bank (a nonvolatile memory 11*b* in the example of FIG. 19) of the user who performed the calibration (ST26). The data registered in the memory bank may be the second calibration result only, which is made based on the first calibration result.

If recalibration is not performed (No in ST32) while the current user continues to wear the goggles (Yes in ST30), steps ST28 to ST32 are repeated. If recalibration is required because of a change in contact between the EOG electrodes of the goggles and the face of the user by, for example, sweating (Yes in ST32), steps ST14 to ST32 are repeated.

If the current user finishes using the goggles (No in ST30) but a different user uses the same goggles (Yes in ST34), steps ST10 to ST34 are repeated. The first and second calibration results are registered in a memory bank (the nonvolatile memory 11*b* in the example of FIG. 19) of the different user who performed the calibration (ST26). If there is not a different user to use the goggles (No in ST34), the process of FIG. 17 ends.

If the calibration is not performed (No in ST12), whether or not calibration data of the current user are registered in the memory bank (11*b* of FIG. 19) is checked (ST40). The check is performed through an AR display of registered user names, for example (and the AR display is performed in, for example, film liquid crystal displays 12L/12R in FIGS. 18 to 21). If there is the name of the current user (which may be a nickname or a user ID code) in the AR display (Yes in ST40), the user refers to the name and selects the item by, for example, closing of the eyes for a few seconds. The calibration data related to the selected item are then used (ST42). If there is not the user name in the AR display (No in ST40), the calibration is skipped and the goggles are used in preliminarily set default condition (ST44).

Figure 19:
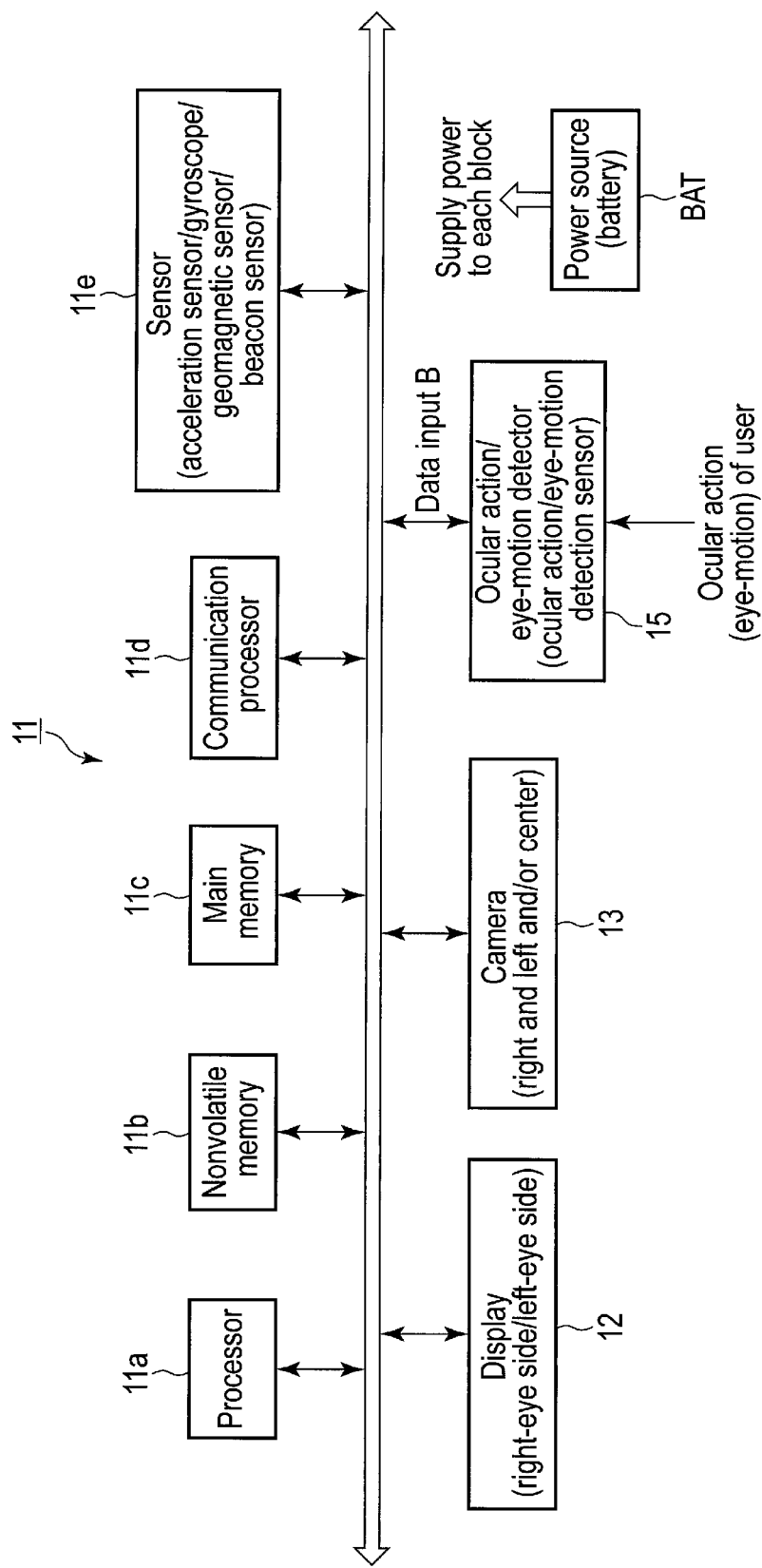
FIG. 19 shows a relationship between a data processor 11 which is attachable to various embodiments and its peripheral devices.

The user who performed the calibration (or user who uses the goggles in the default condition) can provide the data processor 11 of FIG. 19 with instructions corresponding to his-her ocular actions (eye-motion) through the goggles or the like. Now, a case where a camera-equipped remote-controlled robot or a drone is manipulated by the ocular action of the user with the goggles. In that case, the camera direction is moved corresponding to eye movements from the looking straight position to vertical and horizontal directions. The camera zooms in corresponding to a left wink and zooms out corresponding to a right wink. A photo image is taken by two consecutive blinks of the eyes (within one second) (shutter snap). The image taken by the camera can be transferred over Wi-Fi (registered trademark) and/or recorded in a flash memory as JPEG data.

Or, video shooting is initiated by three consecutive blinks of both eyes (within one second). Zoom-in/zoom-out during the shoot can be instructed by a right or left wink. The video shooting is halted by two consecutive blinks of both eyes (within one second) during the shoot. The halt is released by two consecutive blinks of both eyes (within one second) and video shooting is resumed. Closing of the eyes for a few seconds ends the video shooting.

FIG. 18 shows glasses in which electro-oculographic detection electrodes are provided with appropriate positions (corresponding to the example of FIG. 8). In this example, a right lens frame (right rim) 101 and a left lens frame (left rim) 102 are connected by a bridge 103. Right and left lens frames 101 and 102 and bridge 103 are formed of a conductive material, for example, a light metal (such as aluminum alloy and titanium). The left outer side of the left lens frame 102 is connected to a left temple bar 106 through a left hinge 104, and a left tip (left ear pad) 108 is provided with the end of the left temple bar 106. Similarly, the right outer side of the right lens frame 101 is connected to a right temple bar 107 through a right hinge 105, and a right tip (right ear pad) 109 is provided with the end of the right temple bar 107.

The data processor 11 (an integral circuit of a few millimeters square) is embedded in a part of the lens frame 101 in the proximity of the right hinge 105 (or inside the right temple bar 107). The data processor 11 is an LSI including a microprocessor, memory, communication processor, and sensor module including various sensors (the data processor 11 will be described in detail with reference to FIG. 19).

A small battery BAT such as a lithium ion battery is, for example, embedded in the left temple bar 106 in the proximity of the left hinge 104 (or inside the tip 108 or 109) to produce power required for the operation of the eyewear 100.

A left camera 13L is arbitrarily attached to the edge of the left lens frame 102 at the left hinge 104 side, and a right camera 13R is arbitrarily attached to the edge of the right lens frame 101 at the right hinge 105 side. The cameras are ultra-compact CCD image sensors, for example.

The cameras may compose a stereo camera. Alternatively, an infrared camera (13R) and laser (13L) may be provided with the positions of the cameras to compose a distance sensor of a combination of the infrared camera and the laser. The distance sensor may be composed of a small semiconductor microphone (13R) which gathers ultrasonic waves and a small voltage speaker (13L) which irradiates ultrasonic waves, for example.

Note that a center camera may be provided with the bridge 103 instead of or in addition to the right and left cameras 13R/13L. Or, such an eyewear may not include any camera. The cameras are camera 13 in FIG. 19.

A left display 12L is fitted in the left lens frame 102, and a right display 12R is fit in the right lens frame 101. The display is provided with at least one of the right and left lens frames and is formed of film liquid crystal. Specifically, only one or both of the right and left displays 12R and 12L using a film liquid crystal display device adopting polymer dispersion liquid crystal (PDLC) without a polarizer (the displays are display 12 in FIG. 19). If only the display 12R is provided with the right lens frame 101, a transparent plastic plate should be provided with the left lens frame 102.

A nose pad is provided between the right and left lens frames 101 and 102 and below the bridge 103. The nose pad includes a pair of a left nose pad 150L and a right nose pad 150R.

An EOG electrode 151a is arranged on the lens frame 101 to be slantingly above the nose pad 150R. The electrode 151a is formed of a conductive material held by an elastic material. The elastic material may be a soft and suitably elastic material such as sponge or silicon cushion. The conductive material may be a metal (stainless ball) or conductive polymer. Across the right display 12R, an EOG electrode 151b is provided with a position which is symmetrical with respect to the center of the right eye. The electrode 151b is formed of a conductive material held by an elastic material.

Similarly, an EOG electrode 152a is arranged on the lens frame 102 to be slantingly above the nose pad 150L. The electrode 152a is, as with the electrode 151a, formed of a conductive material held by an elastic material. Across the left display 12L, an EOG electrode 152b is provided with a position which is symmetrical with respect to the center of the left eye. The electrode 152b is formed of a conductive material held by an elastic material.

The electrodes 151a and 151b are connected to the positive and negative inputs of ADC 1510 of Ch1, respectively. Similarly, the electrodes 152a and 152b are connected to the positive and negative inputs of ADC 1520 of Ch2, respectively. The electrodes 151b and 152b are connected to the positive and negative inputs of ADC 1512 of Ch0, respectively.

Outputs from the ADCs have different signal wave forms corresponding to the ocular actions (eye-motion) of the user and are supplied to the data processor 11 of FIG. 19 as digital data. The electrodes 151a, 151b, 152a, and 152b are used as eye detection sensors and are components of the ocular action/eye-motion detector 15 of FIG. 19 together with the three AD converters.

FIG. 19 shows a relationship between a data processor (which is an integral circuit including a processor 11a, nonvolatile memory 11b, main memory 11c, communication processor 11d, and sensor 11e, etc.) 11 which is attachable to various embodiments and its peripheral devices (display 12, camera 13, ocular action/eye-motion detector 15, and battery BAT, etc.).

In the example of FIG. 19, the data processor includes, for example, the processor 11a, nonvolatile memory 11b, main memory 11c, communication processor 11d, and sensor lie. The processor 11a is a microprocessor with performance corresponding to a product specification. Various programs executed by the microprocessor and various parameters used for program execution are stored in the nonvolatile memory 11b. A work area used for program execution is provided by the main memory 11c.

The sensor lie includes a sensor group to detect a position and/or direction of the eyewear 100 of FIG. 18, 20, or 21 (frame 110 of FIG. 1, etc.). Specifically, the sensor group includes an acceleration sensor which detects movement along three-axes (x, y, z), gyroscope which detects rotation around three axes, geomagnetism sensor (compass function) which detects an absolute direction, and beacon sensor which obtains positional data and the like by receiving radio and infrared signals. To obtain positional data and the like, iBeacon (registered trademark) and Bluetooth (registered trademark) 4.0 are available.

An LSI used in the data processor 11 is commercially available. For example, wearable device specific TZ1000 series of Toshiba Semiconductor and Storage can be cited. One of the series: TZ1011MBG includes a CPU (11a and 11c), flash memory (11b), Bluetooth Low Energy (registered trademark) (11d), sensor group (acceleration sensor, gyro, and geomagnetism sensor) (11e), 24-bit delta sigma ADC, and I/O (USB and the like).

Commands executed by the processor 11 can be sent from an external server (or a personal computer) which is not shown through the communication processor 11d. The communication processor 11d can use available communication schemes such as ZigBee (registered trademark), Bluetooth (registered trademark), and Wi-Fi (registered trademark). A process result from the processor 11a can be sent to, for example, a server which is not shown through the communication processor 11d.

A system bus of the data processor 11 is connected to a display 12 (12R and 12L), camera 13 (13R and 13L), and ocular action/eye-motion detector 15, for example. Power is supplied to each device (11 to 15) of FIG. 19 by a battery BAT.

The ocular action/eye-motion detector 15 of FIG. 19 includes four ocular action/eye-motion detection electrodes (151a, 151b, 152a, and 152b) of the ocular action/eye-motion detector, three ADCs (1510, 1520, and 1512) which extract digital signals corresponding to ocular actions (eye-motion) from the electrodes, and an output circuit which outputs the data from the ADCs (data corresponding to detection signals waveforms as in FIGS. 11 to 16) to the processor 11a. The processor 11a interprets instructions corresponding to the ocular actions (vertical movement, horizontal movement, blinking, closing of the eyes, and the like) of the user and executes the instructions.

For example, an instruction corresponding to ocular actions (eye-motion) will be performed as follows. Closing of the eyes may be interpreted as selection of a data item currently being seen by the user (as a click of a computer mouse), and consecutive blinks or winks for a few times may be interpreted as execution of the selected data item (as a double-click of a computer mouse). The instruction is an example of data input B using the ocular action/eye-motion detector 15.

FIG. 20 is an example of goggles (in which lens frames of both eyes are formed continuously) 100 as being viewed from the rear. The goggles include EOG electrodes (151a, 151b, 152a, and 152b) of FIG. 2 (or FIG. 8) in the cushion on the frame 110. Film liquid crystal is attached to the lens in the frame 110 to structure a display 12R/12L which provides AR display. The goggles 100 further includes the data processor 11 and battery BAT which are explained with reference to FIG. 19.

FIG. 21 is an example of goggles (in which the lens frames of both eyes are separated) 100 including electro-oculographic detection electrodes provided with appropriate positions on the surface contacting the face of the user (cf. FIG. 8 or the like). The goggles 100 includes displays 12R/12L for AR display, and the data processor 11 and battery BAT which are explained with reference to FIG. 19.

The arrangement of EOG electrodes (151a, 151b, 152a, and 152b) in the goggles 100 of FIG. 21 is similar to that of the glasses of FIG. 18 while the contact between the electrodes and the face of the user is improved in the goggles 100 because of a head strap.

Main Points of Embodiments (1) In an electro-oculographic detector according to an embodiment (FIGS. 1, 2, and 7, etc.), at least four EOG electrodes are arranged around both eyes of a user as follows.

Two electrodes on the left eye side (152a and 152b) and two electrodes on the right eye side (151a and 151b) are arranged symmetrically with respect to a vertical line (e.g., a nose line along the nasal crest of the user) passing the middle point of the line connecting the centers of both eyes.

Two electrodes (151a and 152a) above the line connecting the centers of both eyes and two electrodes (151b and 152b) below the line connecting the centers of both eyes are arranged to avoid a predetermined left area (AXL) including an inflection point where the detection polarity of the electro-oculograph differs in the right and left of a vertical line passing the center of the left eye (P1) and to avoid a predetermined right area (AXR) including an inflection point where the detection polarity of the electro-oculograph differs in the right and left of a vertical line passing the center of the right eye (P2).

(2) In an electro-oculographic detector according to an embodiment (FIG. 2, etc.), at least four EOG electrodes are arranged within a predetermined area corresponding to both eyes of the user (within the shape of the frame 110, for example) as follows, in order to obtain greater ocular action (eye-motion) detection signal amplitude and to eliminate mixture of vertical and horizontal data (data of horizontal eye movements and data of vertical eye movements).

Two electrodes on the left eye side (152a and 152b) and two electrodes on the right eye side (151a and 151b) are arranged symmetrically with respect to a vertical line (a nose line along the nasal crest of the user) passing the middle point of the line connecting the centers of both eyes.

Two electrodes on the left eye side (152a and 152b) are arranged symmetrically with respect to the center of the left eye (P1), and two electrodes on the right eye side (151a and 151b) are arranged symmetrically with respect to the center of the right eye (P2).

Two electrodes (151b and 152b) below the line connecting the centers of both eyes are arranged to avoid (to be outside) the right predetermined area and the left predetermined areas (AXR and AXL). The left predetermined area (AXL) around the center of the left eye (P1) includes an inflection point based on which the detection polarity of the electro-oculograph changes. The right predetermined area (AXR) around the center of the right eye (P2) includes an inflection point based on which the detection polarity of the electro-oculograph changes.

(3) At least two EOG electrodes are arranged to satisfy the following conditions for detection of vertical eye movements (of one or both eyes) (cf. FIGS. 3 to 6).

Two electrodes (151a and 151c) at the right side or two electrodes (152a and 152c) at the left side are arranged symmetrically with respect to the horizontal line connecting the centers of both eyes, and are arranged vertically of the center of the right or left eye and outside the diameter of the eye ball (but as close to the center as possible) (the diameter may be approximately 25 mm as an adult).

(4) At least two electrodes are arranged to satisfy the followings condition for detection of horizontal eye movements (of one or both eyes) (cf. FIGS. 3 and 4).

At least two electrodes are arranged outside the right and left eyes on the horizontal line connecting the centers of both eyes (151b and 152b in the example of FIG. 3 which are arranged with a gap of approximately 90 mm therebetween given that a gap between the centers of both eyes of an adult is approximately 65 mm and the diameter of the eye balls is approximately 25 mm).

(5) At least two electrodes are arranged to satisfy the following condition for detection of horizontal eye movements (cf. 151b and 152b in the examples of FIGS. 2 and 5 and 151b and 152b and/or 151d and 152d in the example of FIG. 6).

As a device with EOG electrodes arranged as above, there are an eyewear put on a user (as in FIGS. 18, 20, and 21, for example) and a device on which a user put his/her face in use (not shown). As a typical example of the eyewear, there is a goggles. As a typical example of the device, there is an eyepiece of a telescope, microscope, and periscope.

By applying the electro-oculographic detection technique described in the above embodiments to goggles (wearable device with a cushion provided with parts contacting the skin of a user), discomfort of the user caused by EOG electrodes contacting the skin can be structurally reduced.

Furthermore, in the goggles, EOG electrodes can be arranged with greater degree of freedom, and the position and the number of electrodes can be optimized. Therefore, the accuracy and reliability of ocular action (eye-motion) detection can be improved.

[1] According to an embodiment, an electro-oculographic detector acquires an electro-oculograph using at least four electrodes (151a, 151b, 152a, and 152b). In the detector, two electrodes on the left eye side (152a and 152b) and two electrodes on the right eye side (151a and 151b) are arranged symmetrically with respect to a vertical line (e.g., a line along the nasal crest of the user) passing the middle point of the line connecting the centers of both eyes. Two electrodes on the left eye side (152a and 152b) are arranged symmetrically with respect to the center of the left eye (P1), and two electrodes on the right eye side (151a and 151b) are arranged symmetrically with respect to the center of the right eye (P2). Two electrodes above the line connecting the centers of both eyes (151a and 152a) and two electrodes below the line connecting the centers of both eyes (151b and 152b) are arranged to avoid a predetermined left area (AXL) including an inflection point where the detection polarity of the electro-oculograph differs in the right and left of a vertical line passing the center of the left eye (P1) and a predetermined right area (AXR) including an inflection point where the detection polarity of the electro-oculograph differs in the right and left of a vertical line passing the center of the right eye (P2). The two lower electrodes (151b and 152b) detect a first channel signal (Ch0 signal of great amplitude) corresponding to horizontal eye movements.

[2] The two electrodes on the right eye side (151a and 151b) detect a second channel signal (Ch1), the two electrodes on the left eye side (152a and 152b) detect a third channel signal (Ch2), and the horizontal eye movement is detected on the basis of the first channel signal (Ch0) during a period (TX20-1 in FIG. 11) in which the second channel signal (Ch1) and the third channel signal (Ch2) become a reverse phase with respect to the eye movement of the horizontal direction.

[3] The two electrodes on the right eye side (151a and 151b) detect a second channel signal (Ch1), the two electrodes on the left eye side (152a and 152b) detect a third channel signal (Ch2), and one or more markers (M01, M02, M11, M12, P1, and P2) are provided with a position being seen by a user when calibration relating to the eye movement (in horizontal and vertical directions) is performed with respect to the first, second, or third channel signal (Ch0, Ch1, or Ch2).

[4] Two electrodes above the line connecting the centers of the both eyes (151a and 152a in FIG. 2) are arranged inside an area between the vertical line passing the center of the left eye (P1) and the vertical line passing the center of the right eye (P2) to avoid the predetermined left area (AXL) and the predetermined right area (AXR).

[5] Two electrodes above the line connecting the centers of the both eyes (151d and 152d in FIG. 6) are arranged outside an area between the vertical line passing the center of the left eye (P1) and the vertical line passing the center of the right eye (P2) to avoid the predetermined left area (AXL) and the predetermined right area (AXR), and the two electrodes above the line connecting the centers of the both eyes (151d and 152d in FIG. 6) detect a fourth channel signal (Ch3).

[6] According to an embodiment, an electro-oculographic detector acquires an electro-oculograph using at least four electro-oculographic electrodes (151a, 151b, 152a, and 152b). In the detector, two electrodes on the left eye side (152a and 152b) and two electrodes on the right eye side (151a and 151b) are arranged symmetrically with respect to a vertical line passing a middle point of a line connecting centers of the both eyes (for example, line along the nasal crest of the user). The two electrodes on the left eye side (152a and 152b) are arranged symmetrically with respect to a center of the left eye (P1). The two electrodes on the right eye side (151a and 151b) are arranged symmetrically with respect to a center of the right eye (P2). Two electrodes below the line connecting the centers of the both eyes (151b and 152b) are arranged with a gap therebetween (124 mm, for example) which is wider than a gap between the centers of the both eyes (65 mm, for example) by a predetermined value or more (50 mm, for example). The two electrodes below the line connecting the centers of the both eyes (151b and 152b) detect a first channel signal corresponding to a horizontal eye movement (Ch0 signal of great amplitude).

[7] The predetermined value is greater than a sum (50 mm, for example) of diameters of the both eyes of an average adult (25 mm, for example).

[8] The two electrodes on the right eye side (151a and 151b) detect a second channel signal (Ch1), the two electrodes on the left eye side (152a and 152b) detect a third channel signal (Ch2), and the first channel signal (Ch0) detects an eye movement of the horizontal direction during a period (TX20-1 in FIG. 11) in which the second channel signal (Ch1) and the third channel signal (Ch2) become a reverse phase with respect to the eye movement horizontally.

[9] The two electrodes on the right eye side (151a and 151b) detect a second channel signal (Ch1), the two electrodes on the left eye side (152a and 152b) detect a third channel signal (Ch2), and one or more markers (M01, M02, M11, M12, P1, and P2) provided with a position being seen by a user when calibration relating to the eye movement (in horizontal and vertical directions) is performed with respect to the first, second, or third channel signal (Ch0, Ch1, or Ch2).

[10] With the device of [1], provided is an eyewear (such as the goggles of FIG. 20) including a frame (110) contacting the face of a user in which the electrodes (151a, 151b, 152a, and 152b) are incorporated.

[11] With the device of [1], provided is a frame (110 of FIG. 2) in which the electrodes (151a, 151b, 152a, and 152b) are incorporated. The frame can be applied to an eyepiece of a device such as a telescope instead of an eyewear.

[12] In the device of [1], a blink, closing of the eyes, horizontal eye movement, vertical eye movement, and right or left wink are detected based on signals (Ch0 signal, Ch1 signal, Ch2 signal) detected by at least two of the at lest four electrodes (151a, 151b, 152a, and 152b).

[13] With the device of [6], provided is an eyewear (such as the goggles of FIG. 20) including a frame (110) contacting the face of a user in which the electrodes (151a, 151b, 152a, and 152b) are incorporated.

[14] With the device of [6], provided is a frame (110 of FIG. 2) in which the electrodes (151a, 151b, 152a, and 152b) are incorporated. The frame can be applied to an eyepiece of a device such as a telescope instead of an eyewear.

[15] In the device of [6], a blink, closing of the eyes, horizontal eye movement, vertical eye movement, and right or left wink are detected based on signals (Ch0 signal, Ch1 signal, Ch2 signal) detected by at least two of the at lest four electrodes (151a, 151b, 152a, and 152b).

[16] A method according to another embodiment uses an electro-oculographic detector comprising at least four electro-oculographic electrodes (151a, 151b, 152a, and 152b). In this detector, two electrodes on the left eye side (152a and 152b) and two electrodes on the right eye side (151a and 151b) are arranged symmetrically with respect to a vertical line passing a middle point of a line connecting centers of the both eyes. Two electrodes below the line connecting the centers of the both eyes (151b and 152b) are arranged to avoid a predetermined left area (AXL) including an inflection point where the detection polarity of the electro-oculograph differs in the right and left of a vertical line passing the center of the left eye (P1) and a predetermined right area (AXR) including an inflection point where the detection polarity of the electro-oculograph differs in the right and left of a vertical line passing the center of the right eye (P2). The method includes detecting a signal (upward Ch0 signal with greater amplitude in period TX20-1 in FIG. 12) of polarity (polarity in a direction of increasing signal level in the example of FIG. 11) corresponding to an eye movement leftward by the two electrodes below the line (151b and 152b), and detecting a signal (downward Ch0 signal with greater amplitude in period TX20-1 in FIG. 12) of opposite polarity (polarity in a direction of decreasing signal level in the example of FIG. 11) corresponding to an eye movement rightward by the two electrodes below the line (151b and 152b).

[17] In the method of [16], calibration (as in FIG. 17) is performed with respect to each user on the basis of the signal detected therein (Ch0 signal with greater amplitude in period TX20-1 in FIG. 12).

Several embodiments have been described above which are merely examples and do not limit the scope of the invention. Above novel embodiments can be achieved in various models, and various omission, substitution, and modification of the embodiments can be performed within the spirit of the invention.

For example, the above explanation of embodiments is presented directed to acquisition of an electro-oculograph of the human eye. However, the embodiments of the present application can be used for the acquisition of an electro-oculograph of an animal having electrically charged eyeballs (such as a chimpanzee).

The embodiments and their variations are encompassed by the scope and outline of the invention and by the inventions recited in claims and their equality. Note that a part or the whole of an embodiment of the disclosed embodiments combined to a part or the whole of another embodiment of the disclosed embodiments will be encompassed by the scope and outline of the invention.

What is claimed is:

1. A method of detecting an electro-oculograph using an electro-oculographic detector comprising at least four electro-oculographic electrodes, wherein
 the at least four electro-oculographic electrodes comprises a first left electrode, a second left electrode, a first right electrode, and a second right electrode;
 the method comprising:
 positioning the first left electrode and the first right electrode above a first line connecting a center of a left eye and a center of a right eye and symmetrically with respect to a first vertical line passing a middle of the first line;
 positioning the second left electrode and the second right electrode below the first line and symmetrically with respect to the first vertical line;
 positioning the second left electrode to avoid a left area including a left inflection point where a detection polarity of an electro-oculograph differs in the right and left of a second vertical line passing the center of the left eye;
 positioning the second right electrode to avoid a right area including a right inflection point where a detection polarity of an electro-oculograph differs in the right and left of a third vertical line passing the center of the right eye;
 positioning the first left electrode to be inside a first area between the second vertical line and the third vertical line and to avoid the left area;
 positioning the first right electrode to be inside the first area and to avoid the right area;
 positioning the first left electrode and the second left electrode symmetrically with respect to the center of the left eye;
 positioning the first right electrode and the second right electrode symmetrically with respect to the center of the right eye, wherein a distance between the second left electrode and the second right electrode is longer than a distance between the center of the left eye and the center of the right eye area;
 detecting by the second left electrode and the second right electrode a first channel signal with respect to an eye movement of a horizontal direction;
 detecting by the first right electrode and the second right electrode a second channel signal;
 detecting by the first left electrode and the second left electrode a third channel signal; and
 detecting the eye movement of the horizontal direction based on the first channel signal during a period wherein a phase of the second channel signal is reversed to a phase of the third channel signal.

2. The method of claim 1, further comprising:
performing calibration of the first channel signal, the second channel signal, and the third channel signal for an ocular action for each user.

3. The method of claim 1, further comprising:
providing one or more markers at a position seen by a user when the calibration is performed.

4. The method of claim 1, further comprising:
detecting a blink, closing of the left eye and the right eye, horizontal eye movement, vertical eye movement, or wink of left eye or the right based on the first channel signal, the second channel signal, and the third channel signal.

* * * * *